(12) United States Patent
McAllister et al.

(10) Patent No.: US 8,529,573 B2
(45) Date of Patent: Sep. 10, 2013

(54) DISTAL FEMORAL CUTTING GUIDE

(76) Inventors: Craig M. McAllister, Kirkland, WA (US); Steven Jacobson, Dupont, WA (US)

( * ) Notice: Subject to any disclaimer, the term of this patent is extended or adjusted under 35 U.S.C. 154(b) by 250 days.

(21) Appl. No.: 13/134,824

(22) Filed: Jun. 16, 2011

(65) Prior Publication Data

US 2011/0251618 A1    Oct. 13, 2011

Related U.S. Application Data

(63) Continuation of application No. 11/800,137, filed on May 4, 2007, now Pat. No. 7,985,226.

(51) Int. Cl.
*A61B 17/58* (2006.01)
*A61B 17/60* (2006.01)
*A61F 2/00* (2006.01)

(52) U.S. Cl.
USPC .............................................. 606/88; 606/89

(58) Field of Classification Search
USPC .............. 606/87–89, 96, 98, 102; 623/20.14, 623/20.19
See application file for complete search history.

(56) References Cited

U.S. PATENT DOCUMENTS

2005/0234466 A1 * 10/2005 Stallings ........................ 606/88

* cited by examiner

*Primary Examiner* — Sameh Boles

(57) ABSTRACT

A device and a method for establishing a position and orientation for a preliminary saw cut in a distal end of a femur to prepare the femur for installation of a prosthetic knee joint. A guide block defining a cutting plane is carried on an adjustably positioned locating arm that is supported on an alignment body that can be mounted on a femur either with or without an intramedullary rod in place in the distal end of the femur. Adjustment screws and horizontal slots in the alignment body provide for varus/valgus angular adjustment of the position of the alignment body. An adjustment guide block may have a saw guiding face defining a differently oriented cutting plane.

16 Claims, 14 Drawing Sheets

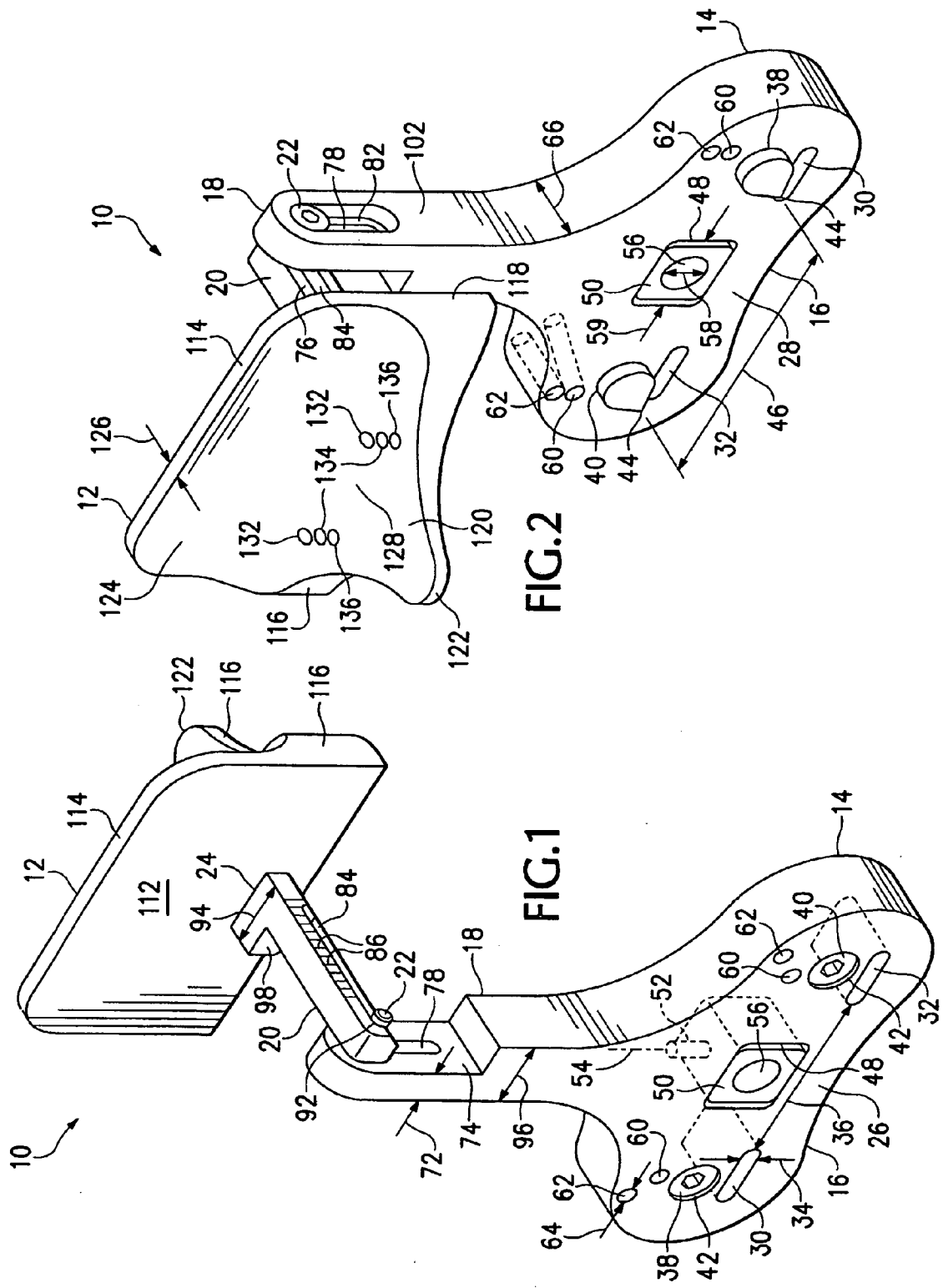

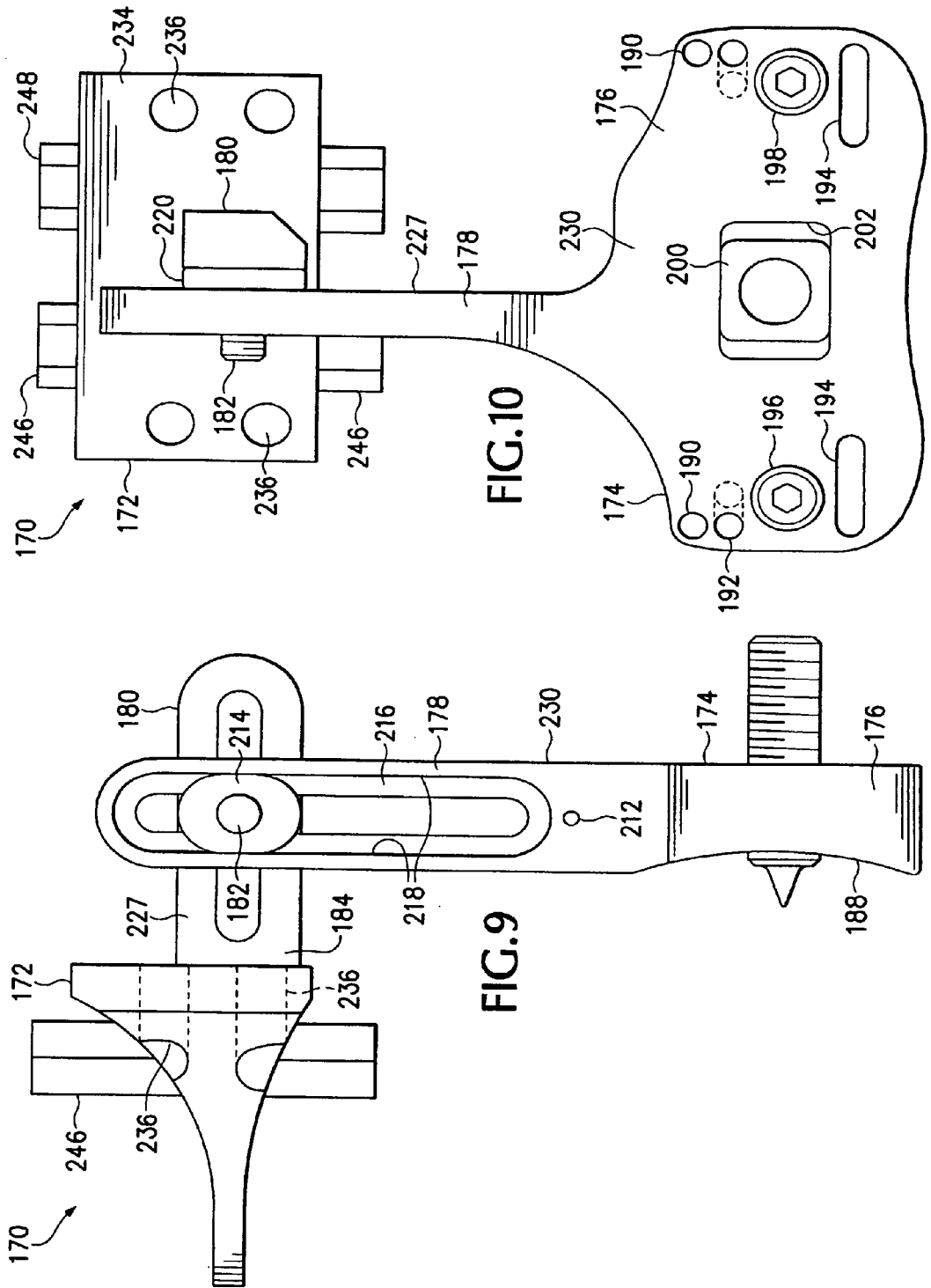

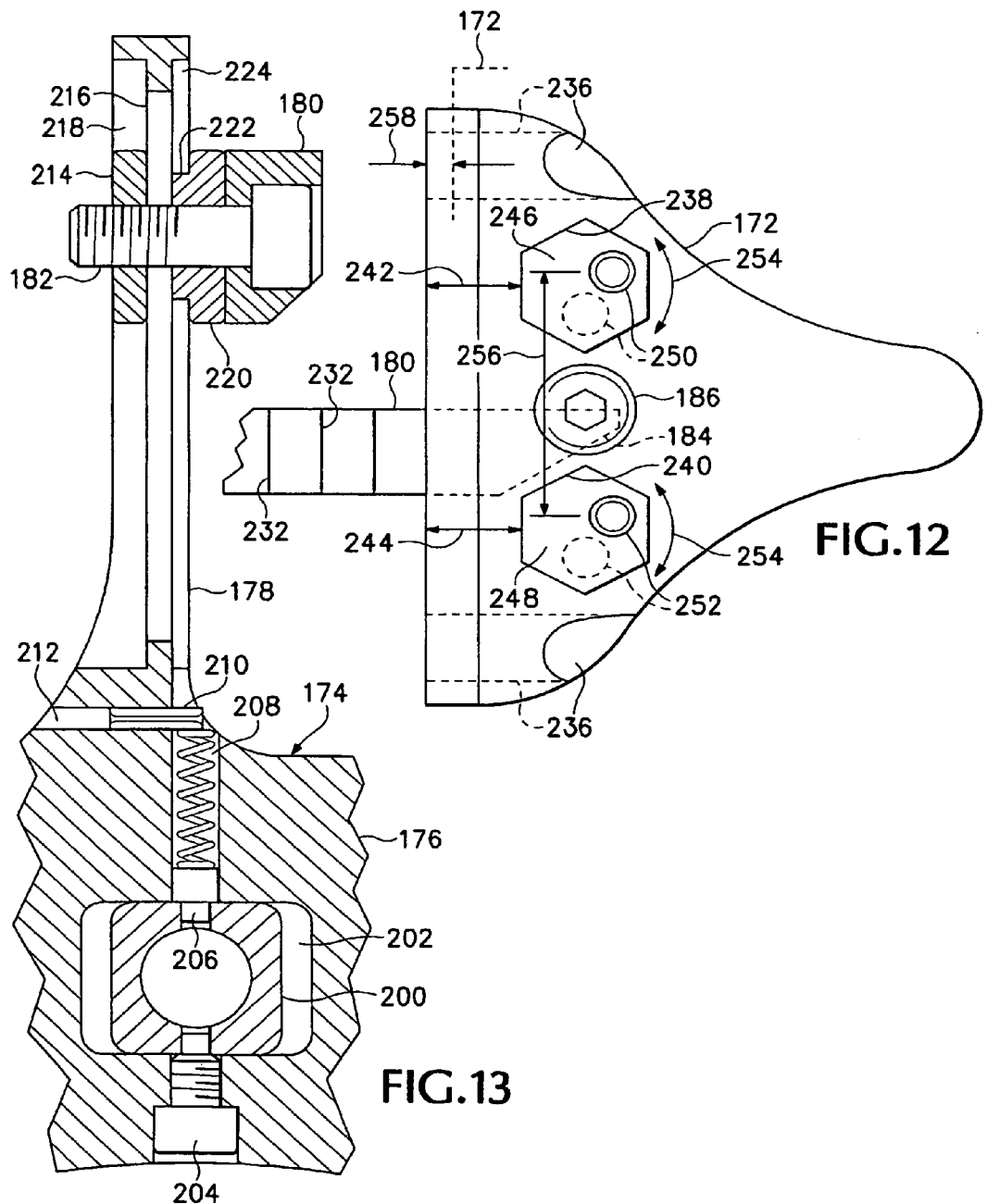

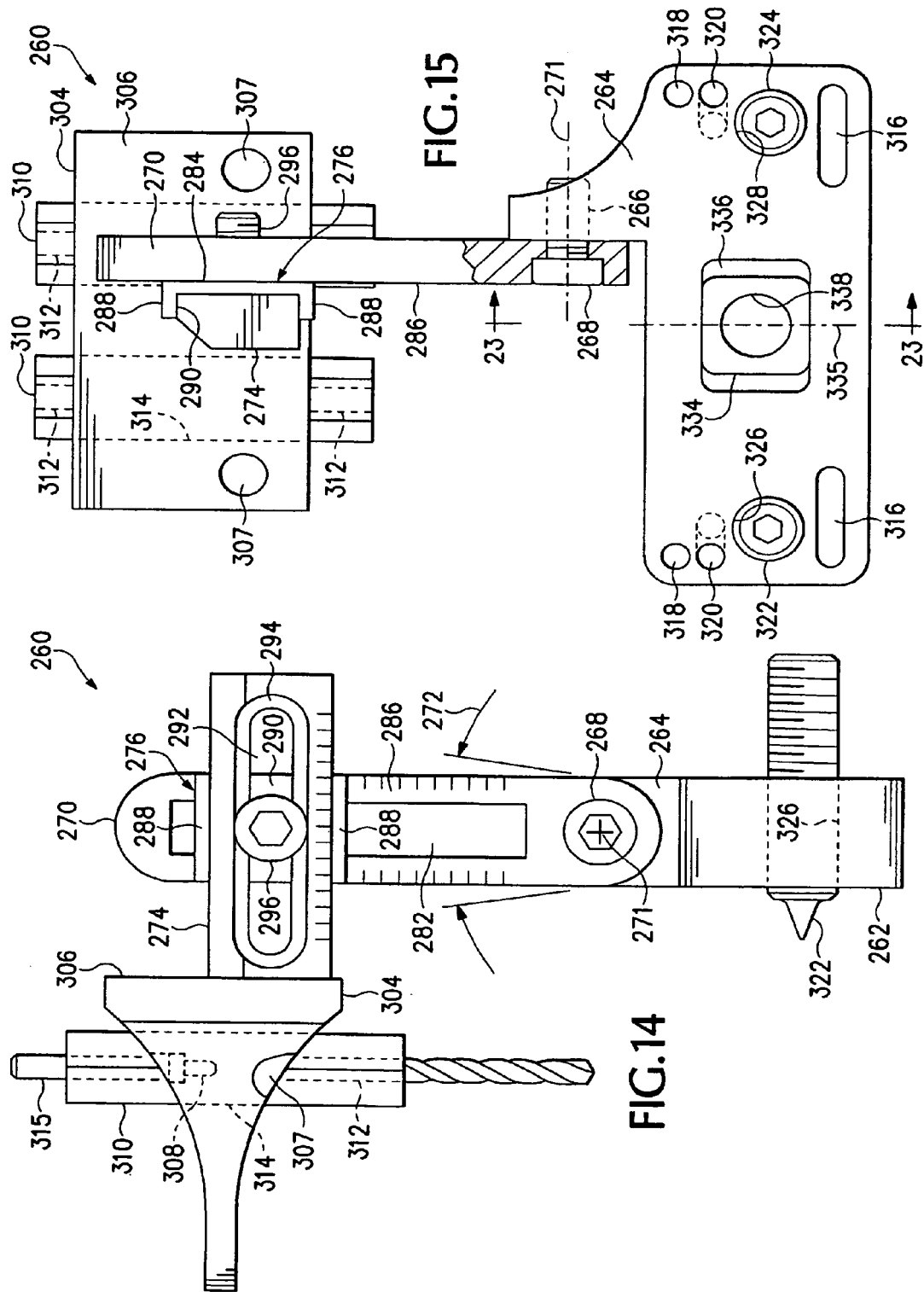

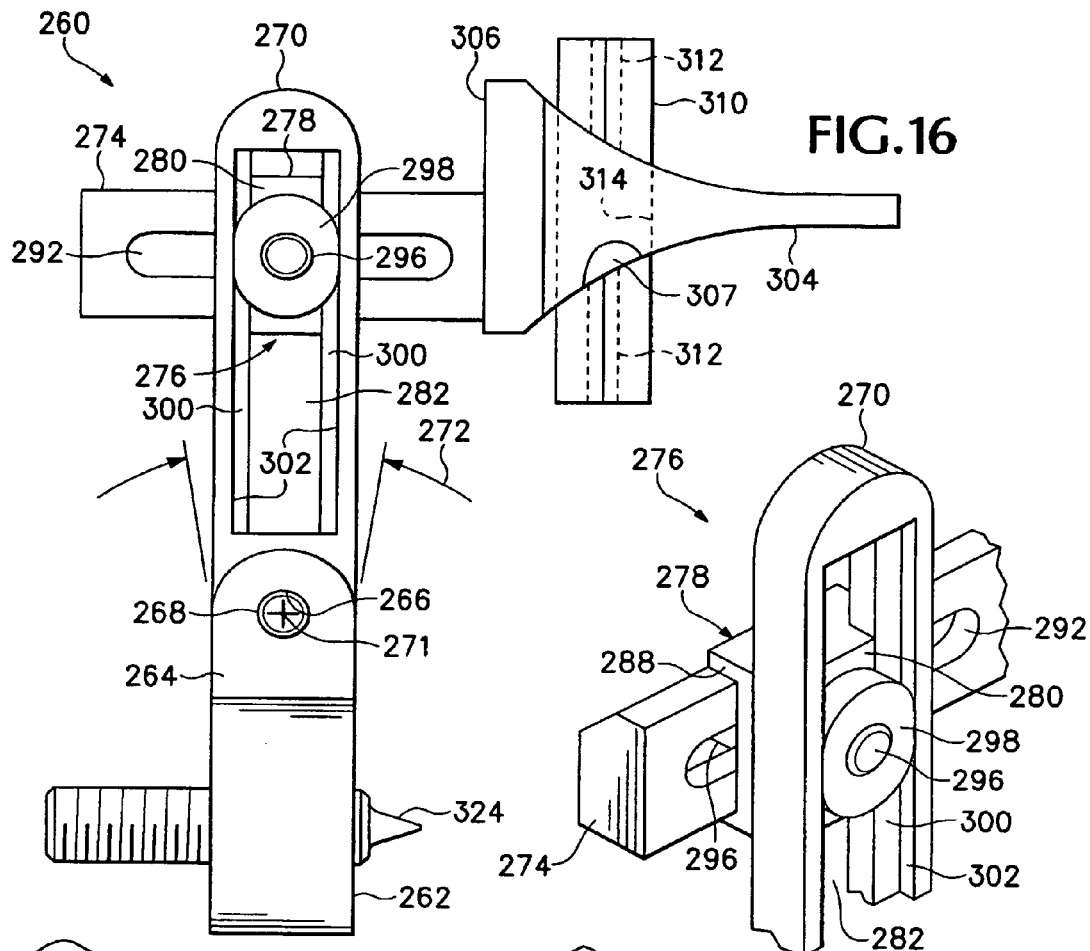
FIG. 16
FIG. 17
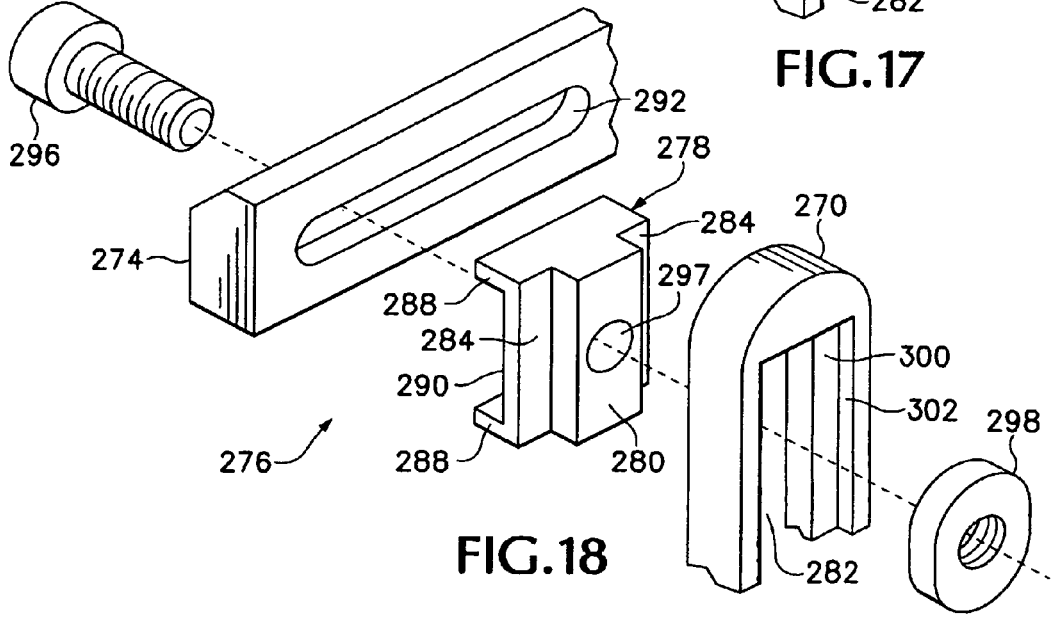
FIG. 18

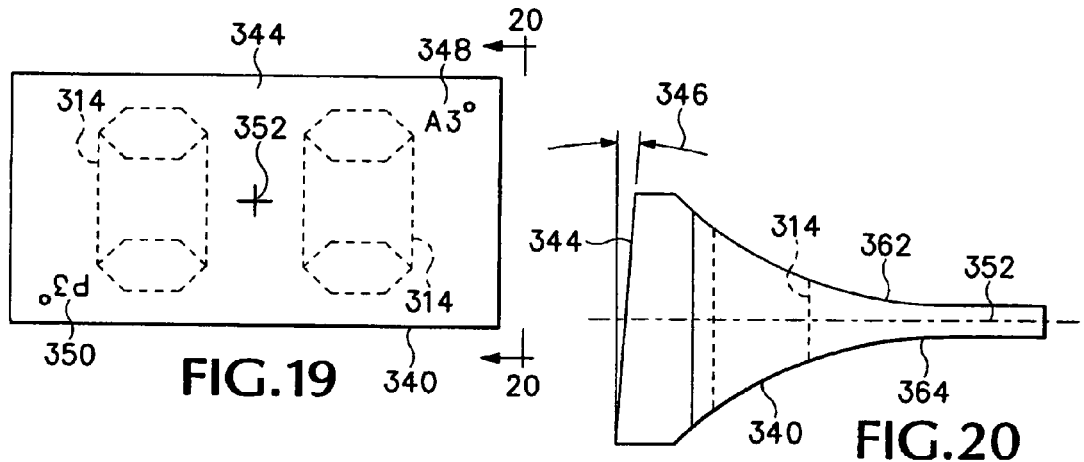
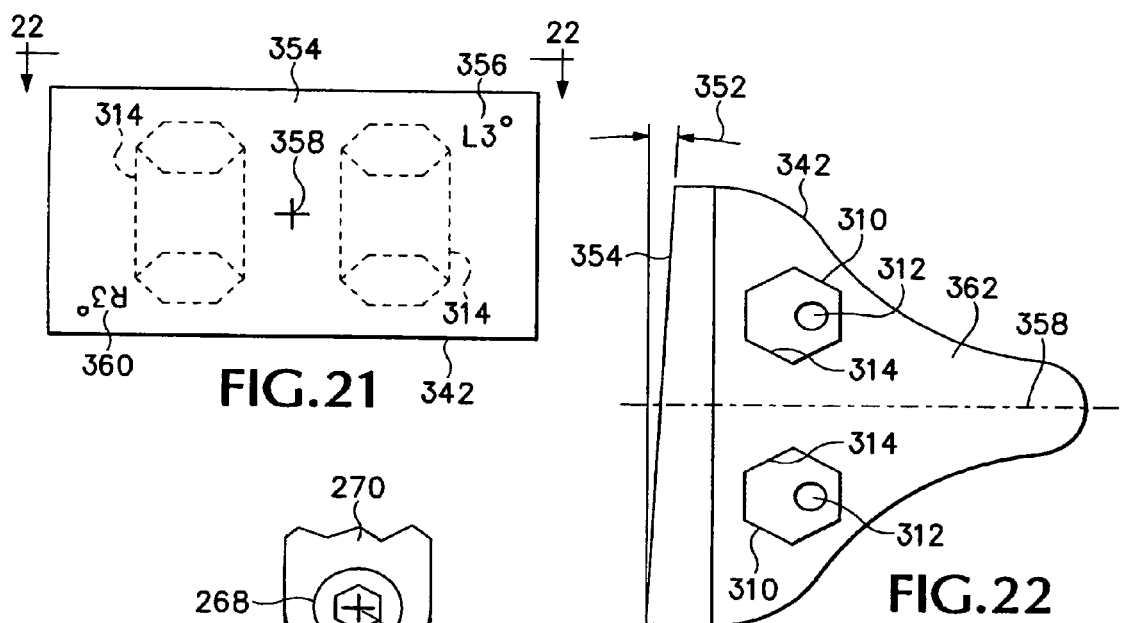
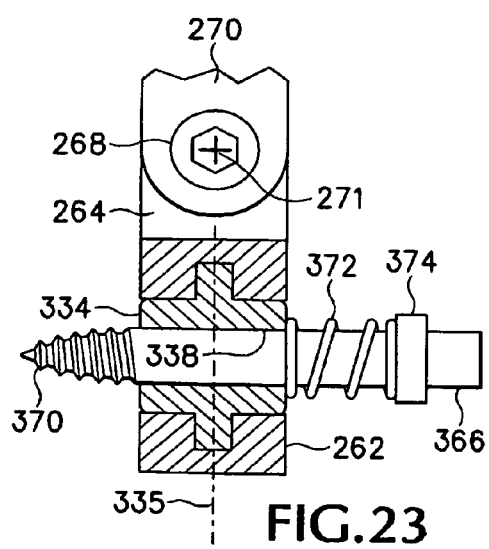

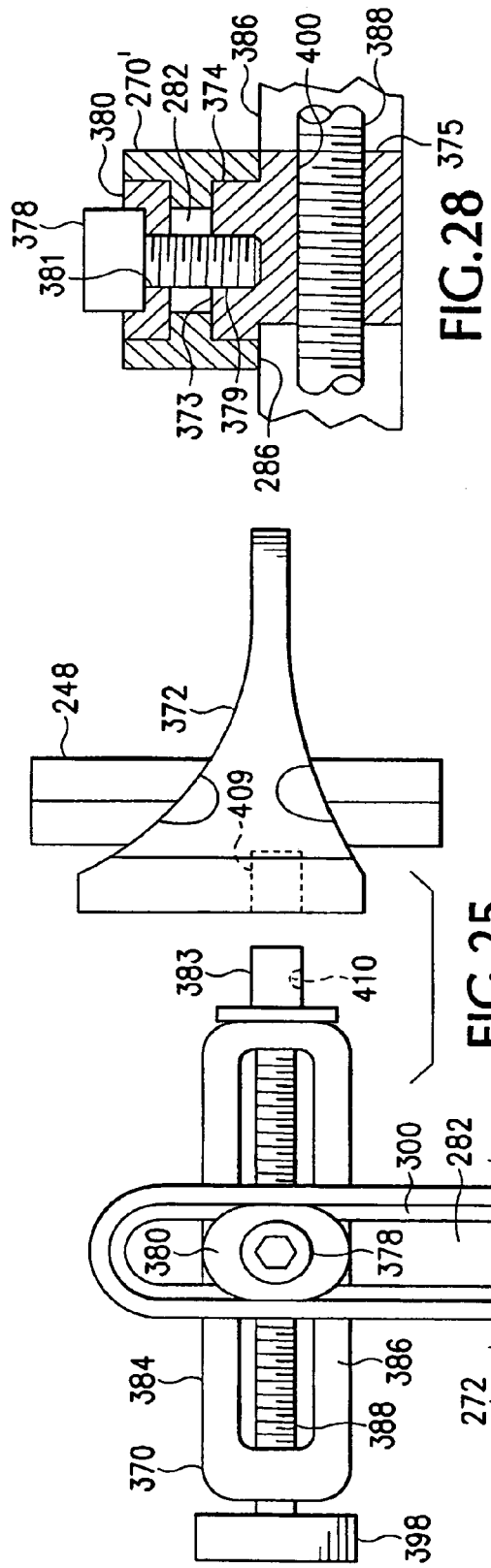

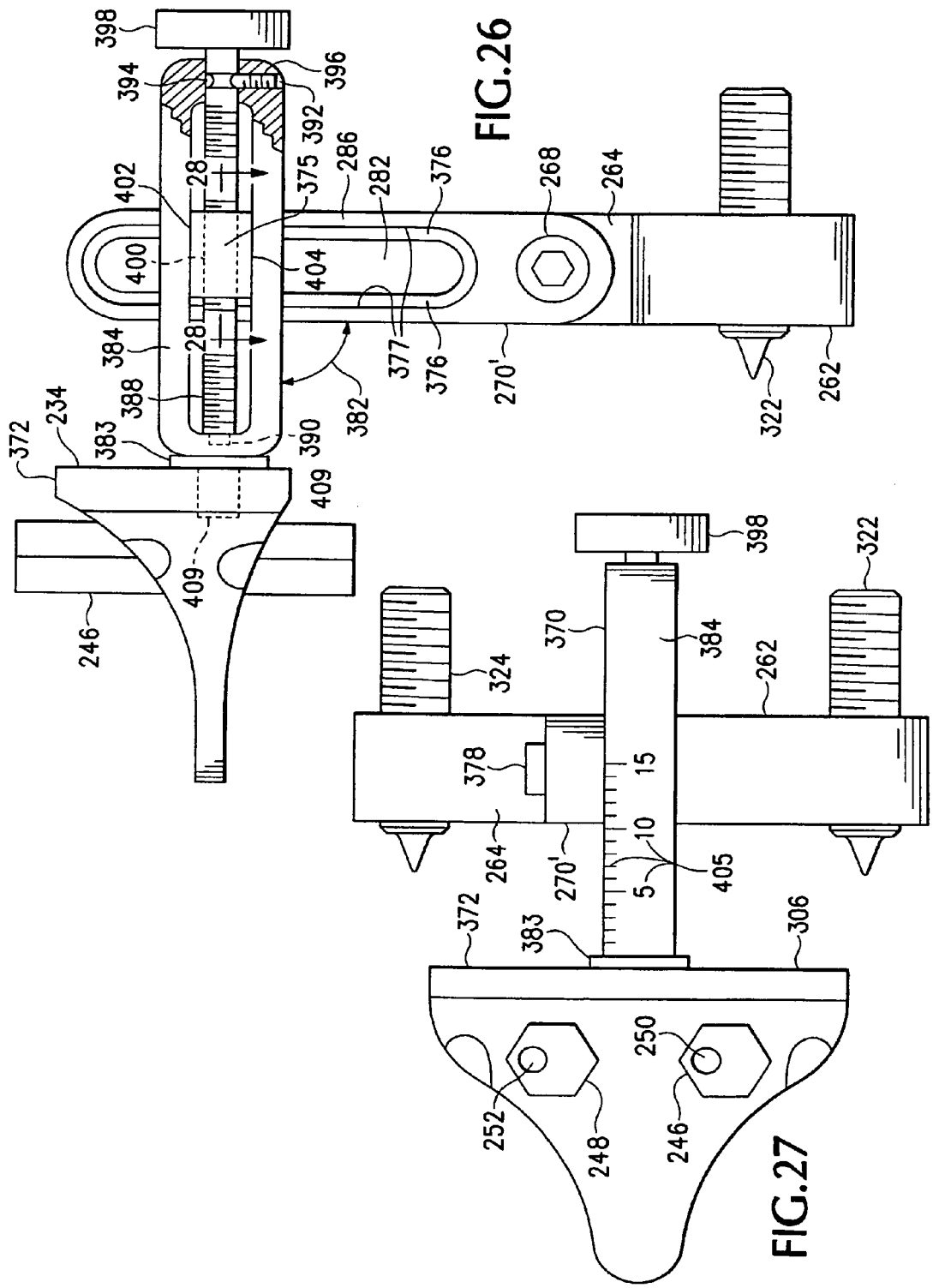

DISTAL FEMORAL CUTTING GUIDE

CROSS REFERENCE TO RELATED APPLICATION

This application is a continuation of U.S. patent application Ser. No. 11/800,137 filed May 4, 2007.

BACKGROUND OF THE INVENTION

The present invention relates to knee replacement surgery, and in particular relates to preparation of the distal end of a patient's femur to receive a part of a prosthetic knee joint.

Surgery to replace an entire knee joint has become relatively common in recent years, and various types of prosthetic knee joints have been designed. Each replacement knee joint requires preparation of the femur and the tibia of the patient to receive portions of the prosthetic joint that operate together to provide mobility approaching that of the patient's natural knee joint. For a replacement knee to operate optimally and for the patient to be able to move with a natural gait, the prosthetic knee joint parts must be installed in precisely the right positions and alignment.

A portion of the distal end of the femur must be removed to provide a seat for the femoral prosthetic part. According to earlier procedures for location of the portions of a prosthetic knee joint, an intramedullary rod is installed in the femur being prepared, and the proper location and orientation of a saw guide is referred to such an intramedullary rod, as taught, for example, by Cripe et al., U.S. Pat. No. 6,193,723.

Dunn et al, U.S. Pat. No. 4,759,350 discloses another cutting guide located on a patient's femur through the use of an intramedullary rod to guide in cutting away portions of the distal end of a femur in order to receive a prosthetic knee joint.

Many patents, including McNulty et al., U.S. Pat. No. 5,688,279, D'Antonio, U.S. Pat. No. 5,810,831, Dunn et al., U.S. Pat. No. 4,759,350, Lackey, U.S. Pat. No. 5,053,037, Hodge, U.S. Pat. No. 5,486,178, Samuelson et al., U.S. Pat. No. 5,611,802, Marik et al., U.S. Pat. No. 5,417,694, and Booth, Jr. et al., U.S. Pat. No. 5,688,280, disclose various devices intended to aid surgeons in properly locating and orienting cuts which must be made to prepare the distal end of the femur to receive the relevant portion of an artificial knee joint.

Recent practice, however, has involved the use of infrared measuring devices communicating with a computer in a navigation system to determine the proper orientation of the femur and tibia with respect to each other and thus to determine the required locations for the portions of a prosthetic knee joint. It has become possible to utilize information determined through use of such an infrared navigating system to locate saw guides used to make an initial cut as part of preparing the distal end of the femur.

For example, the femoral portion of a prosthetic knee joint must be properly aligned with the central longitudinal axis of the femur and must also be oriented at the proper varus/valgus angle with respect to the longitudinal axis of the femur. It must also be mounted in the correct position of rotation about the hinge axis of the prosthetic knee joint to provide for the correct range of articulation.

It is desired, then, to provide a distal femoral cutting guide that can be used either with an intramedullary rod or with the assistance of infrared or other computer-aided navigation methods to locate a guide block properly for making a transverse cut across the condyles of the femur.

SUMMARY OF THE INVENTION

The present invention provides an answer to some of the aforementioned needs for an improved apparatus and method for its use in preparing the distal end of a femur to receive a portion of a prosthetic knee joint, as set forth in the claims appended hereto.

Apparatus according to one preferred embodiment includes an alignment body that is fastened adjustably to the distal end of a femur and which adjustably carries a cutting guide block.

A feature of one preferred embodiment of the apparatus is a varus/valgus adjustment arrangement used to adjust the position of the alignment body with respect to the femur.

A feature of one embodiment of the apparatus is that the alignment body can be attached to a femur either with or without the presence of an intramedullary rod, permitting adjustment of the orientation of a cutting guide block about all axes in either case.

In one embodiment of the apparatus a pair of prism shaped mounting bars fit in corresponding receptacles in the cutting guide block and also fit over mounting pins in an anterior face of a femur so that the position of the cutting guide block can be revised by reorienting the mounting bars on the pins.

In accordance with one embodiment of the method the alignment body is placed adjacent the distal end of a femur, then adjusted in position by rotation about a first axis that is generally parallel with the longitudinal axis of the shaft of the femur, adjusted about an anterior-posterior axis normal to the first axis, to provide a desired varus/valgus-related orientation, and then fixed in place with respect to the femur, after which a cutting guide block attached to the alignment body is rotated as necessary about an axis extending laterally with respect to the femur to establish an orientation of a cut in the femur to provide a desired position of maximum extension of the prosthetic joint.

As another aspect of the method the cutting guide block is thereafter attached to the femur, and the alignment body and a guide block support arm are then separated from the guide block and the femur, leaving the guide block securely located on the femur as a guide for making a properly oriented and unobstructed initial cut to remove portions of the medial and lateral condyles, along a plane extending generally transversely with respect to the longitudinal axis of the femur.

In one embodiment of the method, location of the alignment body with respect to the femur is informed by use of an infrared navigation system including sensors and a computer to refer to the position and orientation of the shaft of the femur.

The foregoing and other objectives, features, and advantages of the invention will be more readily understood upon consideration of the following detailed description of the invention taken in conjunction with the accompanying drawings.

BRIEF DESCRIPTION OF THE DRAWINGS

FIG. 1 is an isometric view, taken from the upper right front of a distal femoral cutting guide which is an exemplary embodiment of the present invention.

FIG. 2 is an isometric view from the upper left rear of the distal femoral cutting guide shown in FIG. 1.

FIG. 9 is a left side elevational view of a distal femoral cutting guide assembly which is an alternative embodiment of the assembly shown in FIGS. 1-8.

FIG. 10 is a front elevational view of the apparatus shown in FIG. 9.

FIG. 12 is a top plan view of the cutting guide block portion of the assembly shown in FIGS. 9-11, taken in the direction indicated by the line 12-12 in FIG. 1, together with a portion of a guide block locating arm in place in the cutting guide block.

FIG. 13 is a fragmentary sectional view taken along the line 13-13 in FIG. 11.

FIG. 14 is a left side elevational view of a distal femoral cutting guide which includes another embodiment of the apparatus disclosed herein.

FIG. 15 is a front elevational view of the distal femoral cutting guide apparatus shown in FIG. 14.

FIG. 16 is a right side elevational view of the distal femoral cutting guide apparatus shown in FIGS. 14 and 15.

FIG. 17 is an isometric view from the upper right front, at an enlarged scale, of a detail of the distal femoral cutting guide assembly shown in FIGS. 14-16.

FIG. 18 is an exploded isometric view of the structures shown in FIG. 17.

FIG. 19 is a front elevational view of a cutting guide block for use in making an adjustment cut at an angle in an anterior or posterior direction.

FIG. 20 is a right side elevational view of the cutting guide block shown in FIG. 19.

FIG. 21 is a front elevational view of a cutting guide block for making an adjustment cut at an angle to the left or right.

FIG. 22 is a top plan view of the cutting guide block shown in FIG. 21.

FIG. 23 is a sectional view of the alignment body shown in FIG. 15, taken along line 23-23, and showing an attachment screw for use with the adjustment body.

FIG. 25 is a right side elevational view of the apparatus shown in FIG. 24, with the cutting guide block shown spaced a small distance apart from the support arm.

FIG. 26 is a left side elevational view of the apparatus shown in FIG. 24.

FIG. 27 is a top plan view of the apparatus shown in FIG. 24.

FIG. 28 is a sectional view of a detail of the cutting guide assembly, taken along line 28-28 in FIG. 26.

FIG. 29 is a front elevational view of the cutting guide block shown in FIGS. 24-26.

FIG. 30 is a sectional view of the cutting guide block shown in FIG. 29, taken along line 30-30, and showing a portion of a guide block support arm, also in sectional view, mated with the cutting guide block.

DETAILED DESCRIPTION OF EMBODIMENTS

Figure 3:
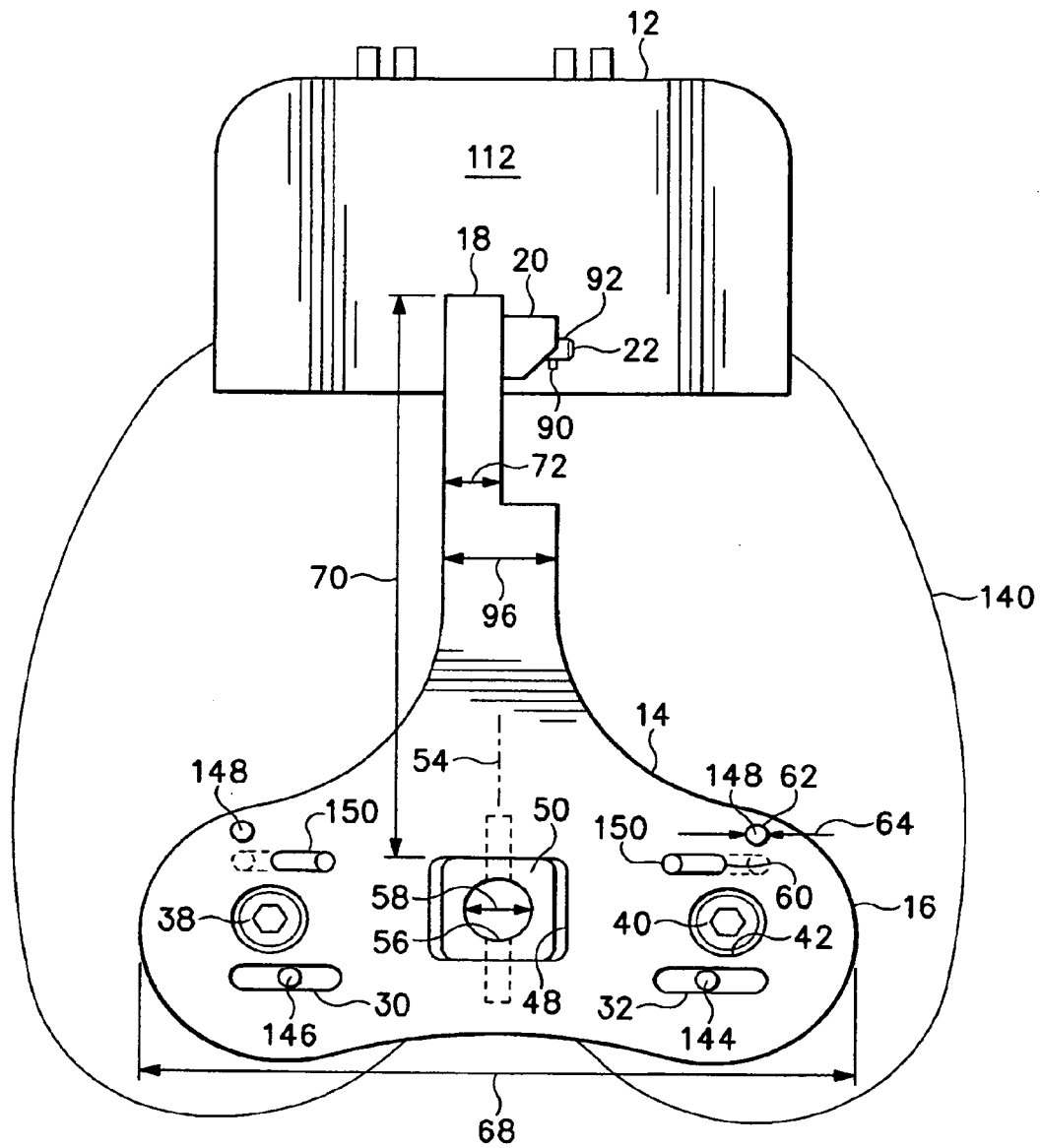
FIG. 3 is a front elevational view of the apparatus shown in FIGS. 1 and 2, showing the guide installed on the distal end of a femur.

Referring now to the drawings which form a part of the disclosure herein, in FIGS. 1 and 2 a distal femoral cutting guide assembly 10 includes a cutting guide block 12 and an alignment body 14. Extending upward from a main or lower portion 16 of the alignment body 14 is a support member 18, which may be an integral part of the alignment body 14. A guide block locating arm 20 is fastened to the support member 18 by a screw or other adjustable fastener 22, and the guide block 12 is mounted removably on the distal, or rear, end 24 of the guide block locating arm 20.

In describing the distal femoral cutting guide disclosed herein, directions such as horizontal, upward or downward, and front and rear will be used in a manner consistent with reference to the distal femoral cutting guide assembly 10 in its ordinary position during performance of total knee replacement surgery, assuming that the patient is supine and the femur is supported in a generally horizontal orientation during the procedure.

The alignment body 14 has a front face 26 and a rear face 28, which in the embodiment shown herein are flat and parallel with each other, although they need not be flat nor parallel with each other. A pair of horizontal slots 30 and 32 extend through the alignment body 14 from the front face 26 to the rear face 28, each slot defining a respective horizontal plane. The slots 30 and 32 are shown as being coplanar, although it is not essential that they be coplanar, provided that they define planes that are parallel with each other. Each of the slots 30 and 32 has a height 34 which may be, for example, about 3.2 millimeters, and each slot 30 or 32 may, for example, be about 11.1 millimeters long, extending laterally on the front face 26. The slots 30 and 32 may be separated from each other laterally of the alignment body 14 by a distance 36 of about 34.9 millimeters, in a distal femoral cutting block assembly 10 intended for use with an average size adult male person, in order to be most effective in fixing the alignment body 14 in a required position with respect to the distal end of a femur.

Spaced a short distance above the horizontal slots 30 and 32 are a pair of varus/valgus adjustment pins 38, 40, each adjustably mated with the alignment body 14, as by threads defined in a respective threaded bore 42, and each extending straight through the alignment body 14. The varus/valgus adjustment pins 38 and 40 may extend proud of the rear face 28 of the alignment body 14, and each preferably has a sharp tip 44, which may be conical, in order to engage a surface of a femur during use of the distal femoral cutting guide assembly so as to prevent the alignment body 14 from moving laterally with respect to the distal end of such a femur, as will be explained in greater detail presently. The bores 42 may be separated from each other laterally in the alignment body 14 by a center-to-center separation 46 of about 51 millimeters, for example, although a different distance 46 may be provided in an alignment body 14 intended for use on smaller or larger femurs.

Located generally centrally in the alignment body 14, and between the bores 42, is a central through-hole 48 extending through the alignment body 14 from its front face 26 to its rear face 28. Within the central through-hole 48 a swivel block 50 is held in place by a pair of pivot pins 52 engaging the alignment body 14 and defining a vertically extending adjustment axis 54 which may be oriented normal to the horizontal planes defined by the slots 30 and 32. The axis 54 provides for rotation of the swivel block 50 with respect to the alignment body 14. The swivel block 50 defines a bore 56 large enough to receive an intramedullary rod (not shown) with an easily sliding yet not loose fit, so that the distal femoral cutting guide assembly 10 can be used in connection with an intramedullary rod (not shown) when desired, although, as will be explained presently, the alignment body 14 can be used independently. Thus the diameter 58 of the bore 56 may, for example, be 7.95 millimeters, while the swivel block 50 is large enough to provide ample strength to hold the pivot pins 52, and to fit snugly between the top and bottom of the through-hole 48. The hole 48 is wider than the swivel block 50 by an amount permitting the swivel block 50 to pivot about the adjustment axis 54 through a small angle, for example, at least about four degrees of arc in either direction, to allow varus/valgus adjustment. Thus, in one embodiment of the alignment body 14, the swivel block 50 may have the general form of a cube about 12.7 millimeters on each side, while the through-hole 48 may have a width 59 of about 15.25 millimeters.

Located above the threaded bores 42 and extending through the alignment body 14 are two pairs of bores, a pair of divergent oblique locating pin holes 60 and, slightly above them, a pair of parallel straight-through locating pin holes 62 which may be normal to the rear face 28 of the alignment body 14. All of the pin holes 60 and 62 extend from the front face 26 through the alignment body 14 to its rear face 28, and all may have the same diameter 64, for example, about 3.2 millimeters, to correspond with commonly used surgical drills and locating pins.

As may be seen in FIG. 3, the oblique locating pin holes 60 are closer together on the front face 26 of the alignment body 14 than are the straight-through locating pin holes 62, although both pairs of holes 60 and 62 are located with equal spacing on the rear face 28. Thus the holes 60 and 62 and the laterally outward end of the horizontal slot 30 or 32 are aligned with each other vertically at the rear face 28 of the alignment body 14, which is shown herein as planar, although planarity is not critical.

For simplicity in manufacture and ease of reference and alignment during use, the alignment body 14 may be of flat plate material such as surgical stainless steel with a thickness 66 of about 12.7 millimeters, for example. The alignment body 14 may, for example, have a width 68 of about 79 millimeters. The shape of the alignment body 14, as seen best in FIG. 3, may resemble an inverted "T" with the ends of its cross member rounded, in order for the alignment body 14 to have ample strength yet not be so large that it would be difficult to use within the available space surrounding an exposed distal femoral end.

The support member 18 portion of the alignment body 14 may extend upward above the main, lower portion 16 of the alignment body 14 to a distance 70 of about 69 millimeters above the through hole 48, with the upper 25 millimeters thereof being reduced to a width 72 of, for example, about 6.35 millimeters. A planar side face 74 of the support member 18 is oriented normal to the rear face 28, defining an alignment plane, and thus, in the embodiment depicted herein, the planar face 74 is also normal to the front face 26 of the alignment body 14 and to the horizontal planes defined by the slots 30 and 32.

As may be seen in FIG. 2, the guide block locating arm 20 has a planar side face 76 resting against the planar face 74 of the support member 18. The fastener 22 holds the guide block locating arm 20 tightly against the support member 18 with the planar faces 74 and 76 in contact with each other, and thus the guide block locating arm 20 is held in a selected position with respect to the support member 18 by friction between the planar faces 74 and 76.

Figure 4:
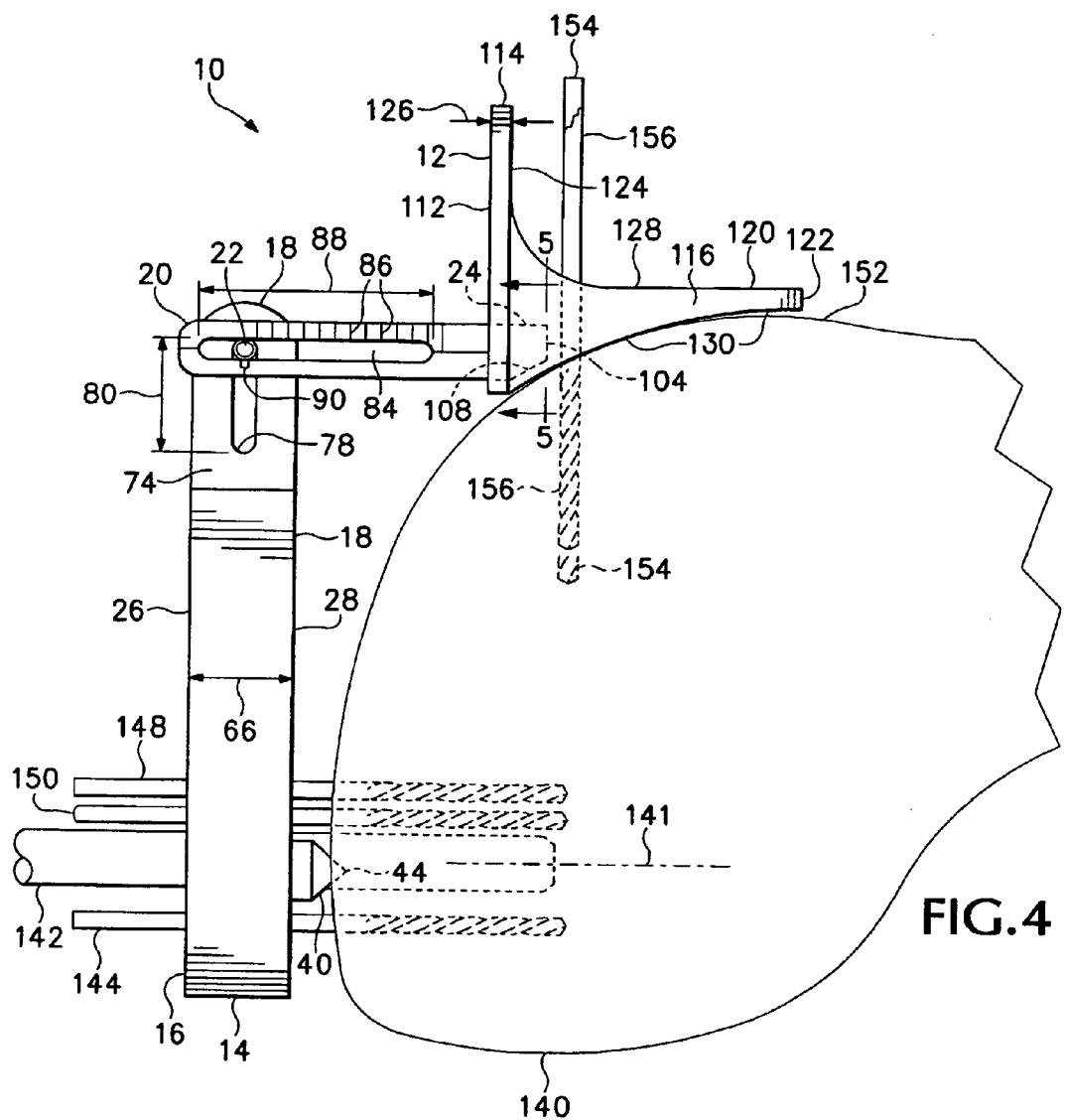
FIG. 4 is a right side elevational view of the distal femoral cutting guide shown in FIGS. 1-3, showing the guide in use to establish the position for a preliminary cut on the distal end of a femur, in preparation for installation of the femoral portion of a prosthetic knee joint.

Referring now also to FIG. 4, it can be seen that a height adjustment slot 78 extends transversely through the narrow upper part of the support member 18. A length 80 of the slot 78 extends vertically, permitting the fastener 22 to move through a distance of about 12.7 millimeters, for example, from top to bottom of the slot 78. As shown in FIG. 2, the head of the fastener 22 may be countersunk within the narrow upper part of the support member 18, being supported by a shoulder 82 defining the slot 78. A corresponding slot 84 is defined in the guide block locating arm 20, extending transversely through the guide block locating arm 20 and extending longitudinally along the guide block locating arm 20. Thus, when the fastener 22 is loosened the guide block locating arm 20 is free to move longitudinally rearward and forward with respect to the support member 18, as well as being able to move upward and downward along the narrow upper part of the support member 18 through the available range of movement of the screw 22 in the slot 78, and being able to rotate in the plane of the faces 74 and 76.

Indicia such as uniformly apart-spaced lines 86 are provided on the guide block locating arm 20, to be used to gauge the distance to which the guide block locating arm 20 is extended beyond the rear face 28 of the alignment body 14. The slot 84 has a length 88 permitting adjustment of the position of the guide block locating arm 20 in a longitudinal direction throughout a range of 25.4 centimeters, for example, in order to be able to support the guide block 12 where necessary to guide a saw to cut through the femur at the required location.

As may be seen best in FIGS. 3 and 4, the fastener 22 fits snugly within the slots 78 and 84, and may include a transversely protruding, small pin 90 to secure a collar 92 and to limit rotation of the fastener 22 between a position of maximum looseness and a position of sufficient tightness. When tightened the fastener 22 holds the guide block 12 and the guide block locating arm 20 with the planar faces 74 and 76 in tight, frictional, contact against each other to support to guide block 12 in a desired location. Thus the fastener 22 may be, for example, a screw mated with threads in the collar 92, or may include a cam acting against the shoulder 82.

Figure 5:
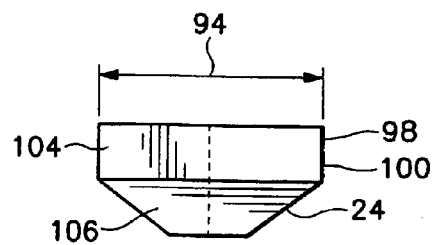
FIG. 5 is a view taken in the direction indicated by line 5-5 in FIG. 4, showing the rear end of the guide block locating arm.

Referring to FIG. 5, the rear end 24 of the guide block locating arm 20 extends to a width 94 equal to the width 96 of the support member 18 below its narrow upper part, with a left leg 98 extending laterally so that a left side 100 is aligned with the left side 102 of the support member 18. A rear end of the arm 20 mates with the guide block 12 and has a rear end face 104 which is rectangular, while a trapezoidal lower rear end face 106 is inclined downwardly away from the rear end face 104 and toward the alignment body 14. A correspondingly shaped receptacle such as a socket 108 is provided in the guide block 12 in the form of a cavity which snugly receives a part of the rear or distal end portion 24 of the guide block locating arm 20, so that the guide block 12 is precisely and stably located on the guide block locating arm 20 when the rear end 24 is fitted matingly in the socket 108 as shown in FIGS. 1-4. The rear end face 104 may be oriented normal to the length of the guide block locating arm 20, and thus parallel with the rear face 28 of the alignment body 14 when the guide block locating arm 20 is located as shown in FIGS. 1-4, oriented normal to the rear face 28 of the alignment body 14. It will be understood that other shapes of the rear end 24 and corresponding shapes of the socket 108 may be used if they can mate so as to hold the guide block 12 stably on the locating arm 20.

The guide block 12 has a planar saw guiding face 112 through which the socket 108 extends. An upper margin 114 of the guide block 12 extends generally horizontally, joining a pair of parallel upright sides 116 and 118 through smoothly arcuate corners, provided in order to avoid having any of a patient's tissue be caught on the guide block 12. A rear portion 120 of the guide block 12 is tapered to a narrow width, with a rounded tip 122 defined at the rear ends of the sides 116 and 118, which extend rearwardly in mirror-opposite ogival shapes, as may be seen in plan view in FIG. 6. An upper rear face portion 124 is flat and generally parallel with the saw guiding face 112, from which it is spaced apart by a thickness 126 sufficient to provide ample strength and rigidity, for example, about 3.2 millimeters. A top surface 128 extends downwardly and rearwardly from the portion 124 toward the tip 122 and may have a concave shape as shown in FIGS. 2 and 4, and may extend laterally to intersect with the sides 116 and 118. A bottom surface 130 is downwardly concave, and may have a transversely oriented non-circular cylindrical shape, as may be seen in FIG. 4, intersecting with the sides 116 and 118.

Figure 6:
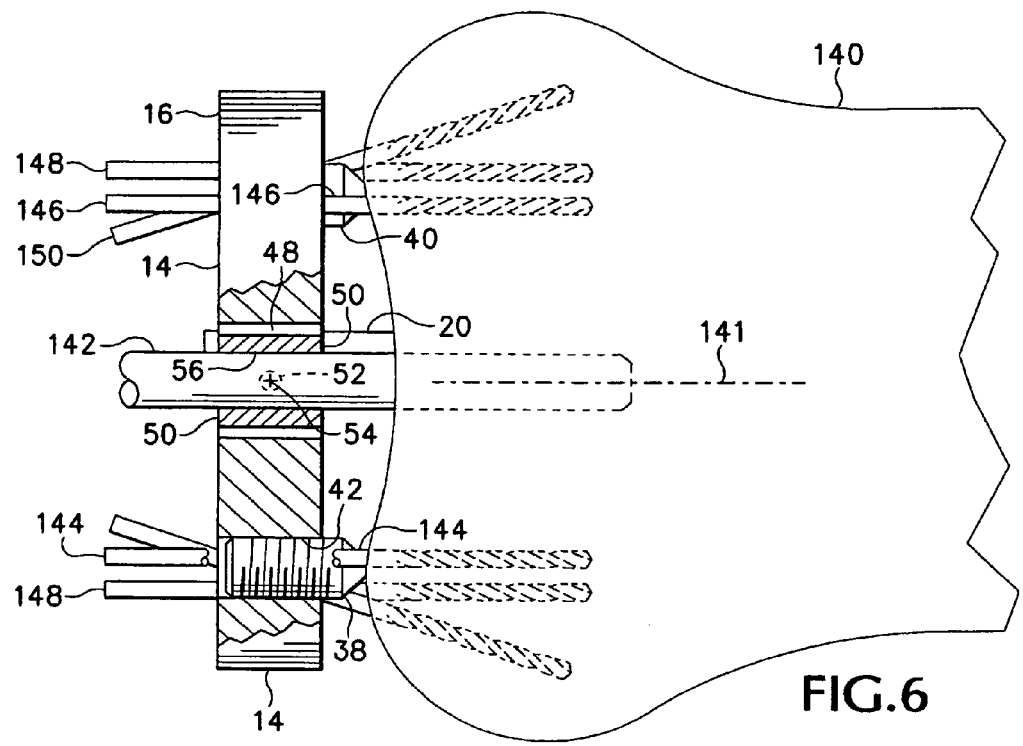
FIG. 6 is a partially cutaway bottom plan view of the distal femoral cutting guide, showing the alignment body fastened to the distal end of a femur to establish a desired position for the cutting guide block.
Figure 7:
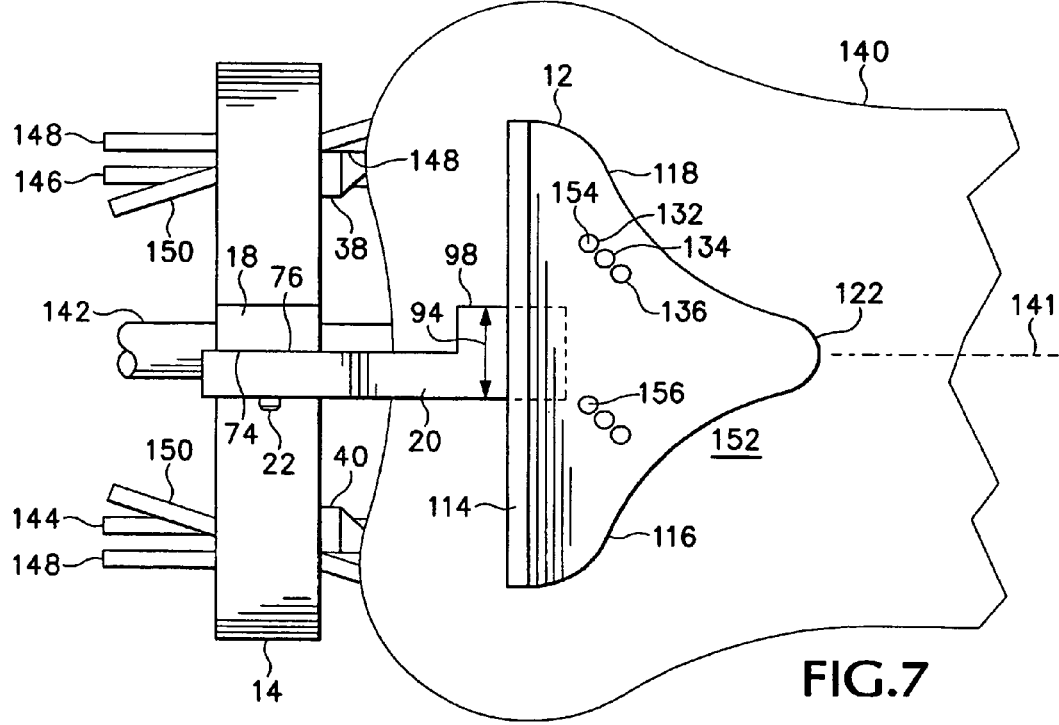
FIG. 7 is a top plan view of the distal femoral cutting guide shown in FIGS. 1-4, together with the distal end of a femur.

Three pairs of mounting pin holes 132, 134, and 136 extend vertically through the guide block 12, parallel with the saw guiding face 112 and with each other, as may be seen in FIGS. 3, 4, and 6. The locations of the pairs 132, 134, and 136 of mounting pin holes are staggered, with the holes of each pair being spaced apart from each other by equal distances, and both holes of each pair being spaced apart from the saw guiding face 112 by equal distances, for reasons which will be understood better in connection with explanation of the use of the cutting guide assembly 10. For example, the holes 132, 134, or 136 of each pair may be separated from each other by a lateral distance 138 of at least about 30 millimeters, to provide stability of the guide block 12 in use. The mounting pin holes 132, 134, and 136 may be similar to the previously mentioned locating pin holes in the alignment body, and thus may have a diameter of, for example, about 3.2 millimeters.

In preparation of the distal end of a femur 140, shown in FIGS. 3, 4, 6, 7, and 8, the distal femoral cutting guide assembly 10 is utilized by placing the alignment body 14 in a selected initial location with its rear face 28 confronting the distal end of the femur 140, with the rear face 28 of the alignment body 14 located closely adjacent to the lateral and medial condyles and oriented approximately normal to the longitudinal axis 141 of the femur 140.

For convenience in illustrating the apparatus, the guide block 12 and guide block locating arm 20 are shown in FIGS. 3 and 4 as being attached to the support member 18, although the locating arm 20 might be removed temporarily from the support member 18 by appropriate manipulation of the screw or other fastener 22 until the position of the alignment body 14 has been adjusted.

The initial position for the alignment body 14 is selected by observation of known anatomical features on the surface of the distal end of the femur 140, as by aligning the through-hole 48 with the location of the intramedullary canal within the femur 140. Alternatively, if an intramedullary rod 142 has already been inserted into the distal end of the femur 140 as shown in FIG. 4, the alignment body 14 is placed adjacent to the distal end of the femur 140 by sliding the swivel block 50 onto and along the intramedullary rod 142, with the rod 142 extending through the bore 56. The alignment body 14 is rotated about the intramedullary rod 142 if it is present, or about an axis generally parallel with the longitudinal axis 141 of the shaft of the femur 140, to a position in which the support member 18 extends toward the anterior face of the distal end of the femur 140, generally along the groove between the lateral and medial condyles. Infrared navigation equipment, in conjunction with computerized locating systems, can also be used to aid in establishment of the best position of rotation of the alignment body 14 about the longitudinal axis 141 of the femur.

Once the alignment body 14 is in the appropriate position of rotation about an intramedullary rod 142 or the longitudinal axis 141, a locating pin 144, which may be in the form of a drill, is inserted through the horizontal slot 30 or the horizontal slot 32, into the distal end of the femur 140, and a second locating pin or drill 146 is inserted through the other one of the horizontal slots 30 and 32, as shown in FIGS. 3, 4, 6, and 7. The locating pins 144 and 146 thus establish a plane in which alignment body 14 can be translated laterally across the distal end of the femur, within the limits established by the locations of the locating pins 144 and 146 in the slots 30 and 32, if there is no intramedullary rod 142 in the bore 56. The alignment body 14 at this point of the procedure also remains free to move in a forward or rearward direction, toward or away from the femur 140, and to rotate to at least a limited degree about an axis parallel with the axis 54 about which the swivel block 50 is free to rotate.

In order to align the pivot axis of the prosthetic knee joint to the femur to give the correct varus/valgus angle, it is necessary to orient the alignment body 14 correctly about the axis 54 or an axis parallel with the axis 54. While the correct alignment can be estimated by the surgeon, the use of computerized infrared navigation or the like can also assist in determining the proper orientation of the alignment body 14, and that orientation can be established and maintained by placing the tips 44 of the varus/valgus adjustment pins 38 and 40 into contact with the surfaces of the distal end of the femur 140, as may best be seen in FIGS. 4, 6, and 7. The adjustment pins 38 and 40 may be extended or retracted appropriately to bring both of the tips 44 into contact with the distal end of the femur 140 to adjust and maintain the orientation of the alignment body 14 with respect to the femur 140. Once the surgeon determines that the alignment body 14 is in, or at least very near, the correct position, a hole is bored into the distal end of the femur 140 through one of the locating pin holes 62 and another locating pin 148 is placed through that locating pin hole 62 into the hole in the femur. This may be repeated using the other locating pin hole 62 and another alignment pin 148. While urging the alignment body 14 toward the femur 140 and maintaining contact of the varus/valgus adjustment pins 38 and 40 against the femur 140, at least one further hole may be bored into the femur, guided by one or each of the obliquely oriented locating pin holes 60, and an alignment pin 150 may then be inserted through that or each locating pin hole 60 into the hole in the femur, effectively preventing the alignment body 14 from thereafter moving with respect to the femur 140.

Thereafter, with the guide block 12 fitted onto the guide block locating arm 20, and with the rear, or distal, end 24 of the locating arm 20 fitted in the socket 108 of the guide block 12, and with the screw or other fastener 22 loosened, the guide block locating arm 20 may be adjusted with respect to the support member 18 to place the saw guiding face 112 at the desired distance from the alignment body 14, using the spaced lines 86 for guidance in movement of the locating arm 20 with respect to the support member 18. Using computer-aided infrared navigation, if available, to determine the correct inclination of the guiding face 112, the fastener 22 may be raised or lowered within the slot 78 as required to permit the bottom face 130 of the guide block 12 to rest upon the anterior face 152 of the distal end of the femur 140, with the guiding face 112 inclined properly about a transverse axis parallel with the fastener 22. This will assure that a cut guided by the guiding face 112 is oriented correctly to receive the femoral portion of a prosthetic knee so as to establish the desired position of full extension. Once the guide block 12 is thus positioned correctly with respect to the anterior face 152 of the femur, holes are drilled into the anterior face 152, guided by selected ones of the mounting pin holes 132, 134, and 136 in the guide block 12, and a pair of mounting pins 154 and 156 are placed into those holes in the femur through respective ones of the holes 132, 134, or 136. Since all of the holes 132, 134, and 136 are parallel with each other, the guide block 12 is free to slide along the mounting pins 154 and 156 into contact with the anterior face 152 of the femur 140, if the guide block when supported by the locating arm 20 is not firmly in contact with the anterior face 152 of the femur 140. If it is determined that the guide block 12 is too near or too far from the distal end of the femur the guide block 12 can be removed from the anterior face 152 by sliding it up along the mounting pins 154 and 156, after which the guide block 12 can be placed adjacent the anterior face by sliding it down along the mounting pins 154 and 156 with the mounting pins extending through a different pair of the holes 132, 134, or 136.

Figure 8:
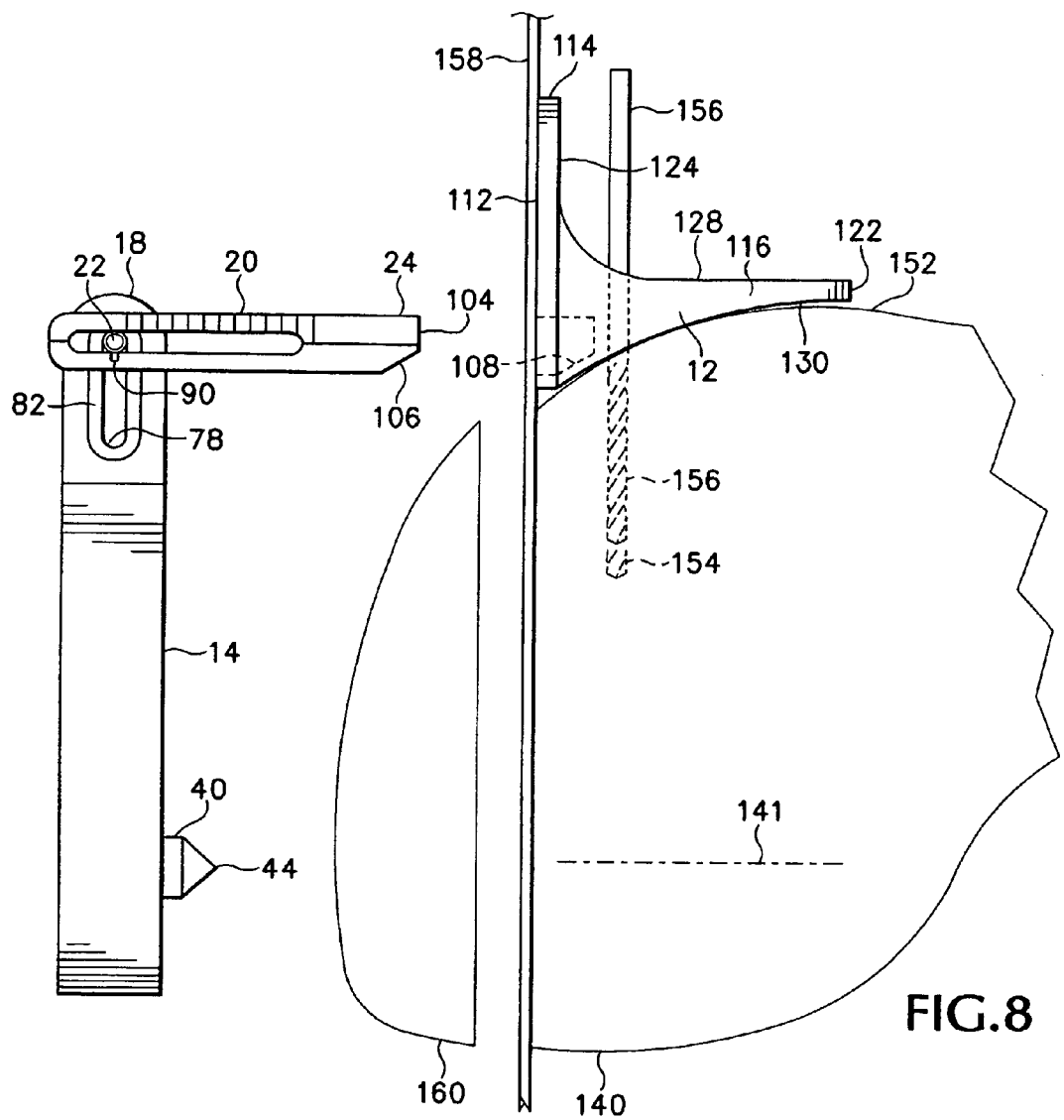
FIG. 8 is a right side elevational view of the distal end of a femur with the guide block installed thereon, showing the alignment body and the guide block locating arm separated from the cutting guide block and showing a saw in use as guided by the guide block.

Once the position of the guide block 12 is thus established, the fastener 22 can be loosened, and the rear end 24 of the guide block locating arm 20 can then be removed from engagement in the socket 108. The alignment body 14 can then be removed from the distal end of the femur 140, by first retracting the locating pin or pins 150 from the oblique hole or holes 60. The locating pins 144, 146, and 148 can then also be retracted and the alignment body 14 can be removed from its position adjacent the femur 140. The intramedullary rod 142, if one had been used, is also removed from the femur 140, and, with the guide block 12 retained on the anterior face 152, a saw 158 may be used as shown in FIG. 8, to cut away the distal end portion 160 of the femur 140 along the optimal plane, guided by the face 112 as shown in FIG. 8.

Referring next to FIGS. 9-12, a distal femoral cutting guide 170 is generally similar to the distal femoral cutting guide assembly 10. The assembly 170 includes a cutting guide block 172 and an alignment body 174 including a lower portion 176 and a support member portion 178. A guide block locating arm 180 is connected with the support member 178 by an adjustment screw 182 or other adjustable fastener, and the cutting guide block 172 is mounted removably on the distal, or rear, end 184 of the locating arm 180, where an attachment screw 186, shown in FIG. 12, is engaged in the guide body 172 and can be tightened to fasten the guide body 172 securely to the locating arm 180.

The alignment body 174 is generally similar to the alignment body 14, but may have a concave rear face 188, as shown herein. The alignment body 174 defines locating pin holes 190 and 192, and slots 194, corresponding to the holes 60 and 62 and slots 30 and 32 in the distal femoral cutting guide assembly 10. Varus/valgus adjustment pins 196 and 198 may be similar to the pins 38 and 40 in the distal femoral cutting guide assembly 10 and are engaged adjustably in threaded holes extending through the alignment body 174.

A swivel block 200 is located within a through-hole 202 defined in the alignment body 174, where it is held in place as shown best in FIG. 13, by a pivot pin 204 in threaded engagement with the alignment body 174 and extending upward into the through-hole 202. A spring-loaded pivot pin 206 is located in a bore 208 and kept in place by a simple fastener such as a roll pin 210 retained in the alignment body 174 as by being press fitted into a transversely extending bore 212. The spring loaded pin 206 utilized in mounting the swivel block 200 conveniently provides some friction against the swivel block 200 yet permits it to move during adjustment of the varus/valgus orientation of the alignment body 174.

Figure 11:
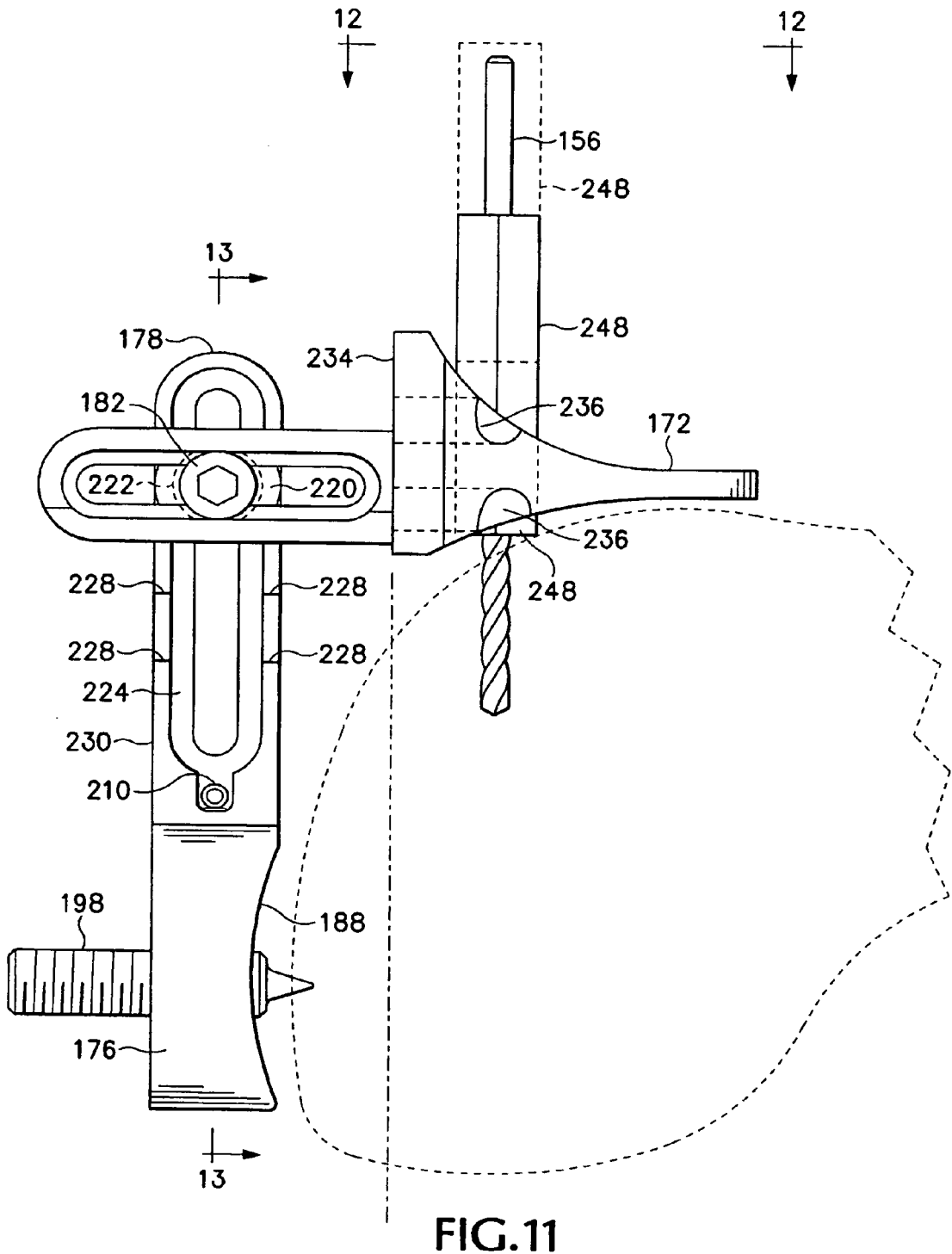
FIG. 11 is a right side elevational view of the apparatus shown in FIGS. 9 and 10, together with a portion of a femur, shown in broken line, with the distal femoral cutting guide in use to establish the position for a preliminary cut on the distal end of the femur, in preparation for installation of the femoral portion of a prosthetic knee joint.
Figure 24:
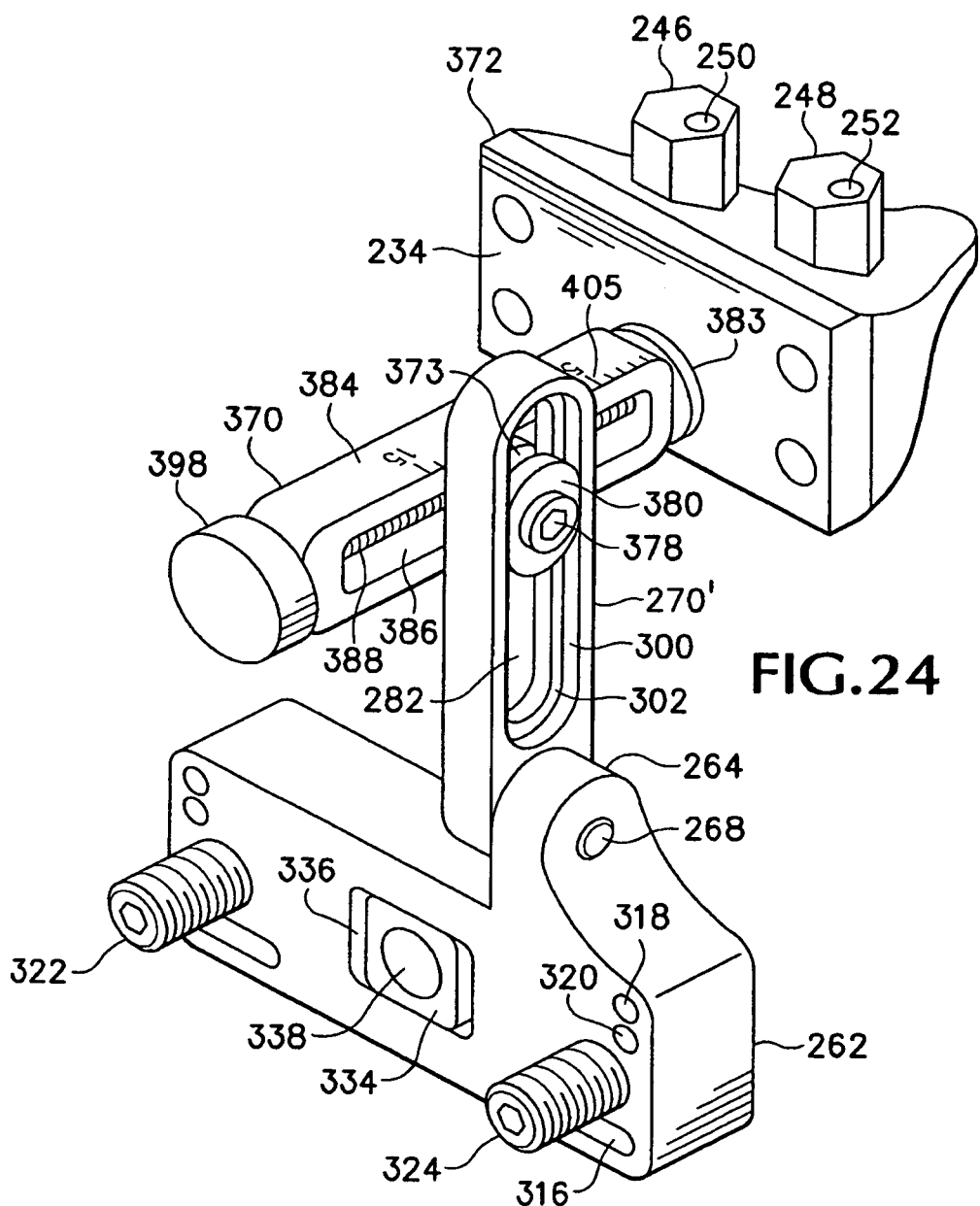
FIG. 24 is an isometric view from the upper right front of a distal femoral cutting guide which is another alternative embodiment of the apparatus shown in FIGS. 1 and 10.

As may be seen most clearly by reference to FIGS. 9, 11, and 13, the guide block locating arm 180 is attached adjustably to the support member 178 by threaded engagement of the adjustment screw 182 with a nut 214, which is located in a recessed slideway 216 defined in the lateral side of the support member 178. The nut 214 is shaped so that it can slide along the slideway 216, but it is prevented from rotating by engagement of its sides with the lateral surfaces 218 that define the slideway.

A washer 220 may be located between the locating arm 180 and the medial side of the support member 178, and may include a reduced diameter portion 222 fitted within a guide channel 224 defined in the medial side 226 of the support member 178, the side that faces toward the cutting guide block locating arm 180. The washer 220 may be made of a suitably hard plastics material, for example, so as to be compressible enough to provide firm frictional contact with both the support member 178 and the opposed planar face 227 of the cutting guide block locating arm 180 to hold the arm 180 securely with respect to the support member 178 when the screw 182 is tightened into the nut 214.

Indicia may be provided on the medial side 226 of the support member 128, as at 228, to indicate when the locating arm 180 is perpendicular to the front face 230 of the alignment body 174. Indicia such as lines shown at 232 may also be provided on the top of the guide block locating arm 180, as may be seen in FIG. 12, to indicate the distance between the support member 178 and the saw guiding face 234 of the cutting guide block 174.

While the overall configuration of the cutting guide block 172 is similar to that of the guide block 12, there are also bores 236 defined in the cutting guide block 172, extending to the saw guiding face 234, as locations for installation of computer-aided infrared or electromagnetic navigation system components that can be used to provide information useful in proper placement of the saw cutting guide block 172. While the bores 236 are shown herein as all being of the same size, it will be understood that bores 236 may be provided in different configurations to accommodate different navigation system components.

The cutting guide block 172 defines a pair of mounting bar holes, receptacles in the form of through-holes 238 and 240, shown herein as being in the shape of regular hexagons. The through-holes 238 and 240 are parallel with each other and with the saw guiding face 234, and are separated from the saw guiding face 234 by equal distances 242 and 244, respectively.

Fitting slidably within the through-holes 238 and 240 are respective hexagonal mounting bars 246 and 248, and each of the mounting bars 246 and 248 defines a respective mounting pin hole 250, 252. Each mounting pin hole 250 or 252 is located eccentrically within the respective mounting bar 246 or 248 and extends entirely through the respective mounting bar from end to end, oriented parallel with the respective mounting bar, so that with the mounting bars 246, 248 in place in the through-holes 238 and 240 the mounting pin holes 250 and 252 are parallel with each other and with the saw guiding face 234. Since the mounting bars 246, 248 and through-holes 238, 240 are shaped as regular prisms, the mounting bars 246 and 248 can be located in the through-holes 238 and 240 in any of six positions of rotation, as indicated by the arrows 254.

By placing both of the mounting bars with similar orientations of the eccentric mounting pin holes 250 and 252, the orientation of the cutting guide block 172 can be maintained while its position is adjusted by reorienting the mounting bars 246, 248 equally. When each mounting bar 246, 248 is rotated clockwise 120 degrees, for example, the mounting pin holes 250 and 252 will be located in the positions shown in broken line in FIG. 12, so that the mounting pin holes remain parallel with each other and separated from each other by the same distance 256, and a plane defined by the mounting pin holes 250 and 252 remains in the same orientation with respect to the saw guiding face 234. It will be understood that any regular prismatic shape might be used for the mounting bars and the corresponding through-holes in the guide block 172, depending upon the number of incrementally different positions desired to be provided. Thus triangular, or square, mounting bars would be useful instead of the hexagonal bars shown.

Use of the distal femoral cutting guide assembly 170 is generally similar to that described above with respect to the distal femoral cutting guide assembly 10. The use of the mounting bars 246 and 248 in conjunction with the through-holes 238 and 240, however, permits adjustment of the position of the cutting guide block 172 with respect to the femur without having to raise the guide block 172 away from the femur in the same fashion as necessary with the guide block 12, since the mounting bars 246 and 248 can be raised along respective mounting pins such as the mounting pins 154 and 156 shown in FIG. 8 in connection with the guide block 12, remaining on the mounting pins.

Once the locating arm 180 has been removed from the guide block 172 the guide block 172 is free to slide downward along the mounting bars 246 and 248 until it comes into contact with the anterior face 152 of the femur. The position of the guide block 172 can thus be adjusted by raising the mounting bars 246 and 248 to clear the top of the guide body 172 as shown in FIG. 11 in broken line. With each mounting bar 246, 248 rotated in the same direction an equal distance to an available mating position within the respective through-hole 238 or 240, the cutting guide block 172 can be moved an incremental distance to permit reinsertion of the mounting bars 246, 248 into the through-holes 238, 240 more simply than by removing the guide block from the mounting pins. Rotation of the mounting bar 246, 248 to the orientation indicated by the positions of the mounting pin holes 250 and 252 as shown in broken line in FIG. 12 would thus result in movement of the cutting guide block 172 to the position shown partially in broken line in FIG. 12, resulting in displacement of the saw guiding face 234 proximally along the femur through the short distance 258 as shown in FIG. 12, while incidentally also moving the cutting guide block 172 laterally, and without reorientation of the saw guiding face 234.

Referring next to FIGS. 14-18, a distal femoral cutting guide 260 has an alignment body 262 that is generally rectangular and more compact than the alignment body 14 or the alignment body 174 described above. An upwardly extending arm 264 includes a threaded hole 266 to receive a screw 268 used to attach an upwardly extending support member 270 to the arm 264. When the screw 268 is loosened the support member 270 may be adjusted angularly about a horizontal axis 271 defined by the screw 268 through an angle 272 with respect to the alignment body 262, as will be explained more fully presently. A generally horizontally extending guide block locating arm 274 is mounted on a sliding support assembly 276 including a slide body 278 that includes a protruding rectangular central portion 280 that fits in the slot 282 defined by the upwardly extending support member 270. A pair of shoulders 284 of the slide body 278 rest against the medial face 286 of the upwardly extending support member 270. A pair of ribs 288 extend horizontally protrude and away from the medial face 286, and, together with a generally planar vertical surface parallel with the medial face 286, form a channel 290 in which the guide block locating arm 274 is held slidably. The slide body 278 thus keeps the guide block locating arm 274 oriented at right angles with respect to the support member 270, while allowing it to be moved up or down along the support member 270.

A slot 292 extends through and along the guide block locating arm 274, and a recessed shoulder 294 surrounds the slot 292 on the left, or medial, side of the guide block locating arm 274. The head of a screw 296 engages the shoulder 294, while the threaded body of the screw extends through the slots 292 and 282 and through a hole 297 that extends through the slide body 278, and the screw 296 is mated with the threads of a nut 298 riding on shoulders 300 recessed in the right, or lateral, side of the support member 270. The support member 270 thus defines rails 302 extending alongside the shoulders 300, and the nut 298 fits closely enough alongside the rails 302 so that the nut 298 is prevented from rotating, although it remains free to move along the rails 302 with the slide body 278 and the screw 296.

With the screw 296 loosened slightly, the guide block locating arm can be moved up and down along the support member 270 along with the slide body 278 and can be moved longitudinally within the channel 290 in a forward or rearward direction with respect to the alignment body 262. Thus, once the support member 270 has been placed at the selected angle 272 with respect to the alignment body 262, the guide block locating arm 274 can be moved with respect to the support member 270 to place the guide block 304 in a desired location. The angle 272 of the support member 270 about the axis 271, with respect to the alignment body 262, is determined by the surgeon to establish a desired posterior/anterior angle of extension for the prosthetic knee joint, and the position of the guide block 304 relative to the anterior face 152 of the femur can be adjusted easily without varying the orientation of the saw guiding face 306 unintentionally.

A screw 308 may be threaded into the cutting guide block 304 and tightened into contact with the top of the guide block locating arm 274 to keep the cutting guide block 304 located properly on the guide block locating arm 274 until the guide block is attached to the femur, as will be explained presently. Hexagonal mounting bars 310 similar to the hexagonal mounting bars 246 and 248, and also including eccentrically located mounting pin holes 312, fit slidably within corresponding receptacles in the form of hexagonal holes 314 extending parallel with each other and the saw guiding face 306 of the cutting guide block 304, so that any pair of correspondingly located longitudinal axes of the hexagonal mounting bars 310 define a plane parallel with the saw guiding face 306, as shown herein. It will be understood that the locations of the hexagonal holes 314 might be arranged otherwise, and that the hexagonal holes 314 might be oriented otherwise than shown herein, or that the bars 310 and the corresponding holes 314 might be of a different regular polygonal cross-section shape, as by being pentagonal or square in cross section.

Similar to the alignment body 14 and the alignment body 174, the alignment body 262 includes horizontal slots 316, and may include straight pin holes 318 and oblique pin holes 320, and a pair of varus/valgus adjustment pins 322 and 324 are mated in corresponding bores 326 and 328. Similarly, a swivel block 334 is mounted to pivot on an adjustment axis 335 in a through-hole 336 in the alignment body 262 and defines a bore 338 similar to the bore 56 through the swivel block 50, capable of snugly but slidably receiving an intramedullary rod.

Sockets 307 may be located on the saw guiding face 306 of the cutting guide block 304 and extend into the cutting guide block 304, as shown best in FIG. 15, to receive and hold suitable infrared computer-aided navigation beacons or other desired devices.

The distal femoral cutting guide assembly 260 may be used in a manner basically similar to the use of the distal femoral cutting guide assembly 170 described above. Once the alignment body 262 is located on the distal end of the femur it is adjusted for varus/valgus angle using the adjusting pins 322 and 324, and mounting pins may be inserted through selected ones of the slots 316 and holes 318 and 320 to keep the alignment body 262 in the adjusted varus/valgus position. The swivel block 334 may also be utilized with an intramedullary rod in the same manner as that described with respect to the swivel block 50 or the swivel block 200. Thereafter, the support member 270 may be rotated to an appropriate angle 272 about the horizontal axis 271. The screw 268 can then be tightened to hold the support member 270 at the selected angle 272 with respect to the alignment body 262 to provide the anterior-posterior angular orientation of the saw guiding face 306 thought to be correct. The guide block locating arm 274 and the sliding support 276 are then raised or lowered along the support member 270 and the guide block locating arm 274 is adjusted rearwardly or forwardly in the channel 290 of the slide body 278 as appropriate to place the cutting guide block 304 correctly adjacent to the anterior face 152 of the distal end of the femur 140, as shown in FIGS. 3, 4, and 11 with respect to the cutting guide blocks 12 and 172.

Once the cutting guide block 304 is in the desired location with respect to the distal end of the femur and is properly aligned as described above, holes are drilled into the anterior face of the femur, guided by the mounting pin holes 312 in the hexagonal mounting bars 310. The drills used may be left in the femur, extending through the mounting pin holes 312 in the hexagonal mounting bars 310 to serve as mounting pins 315.

Once the mounting pin holes are drilled into the anterior face 152 of the femur, with the drills extending as mounting pins 315 through the mounting pin holes 312 in the hexagonal mounting bars 310 and with the cutting guide block 304 attached to the anterior face of the distal end of the femur, the guide block locating arm 274 may be released from the cutting guide block 304, and the alignment body 262 may be removed from the femur.

When the guide block locating arm 274 has been removed the guide block 304 can be slid down along the hexagonal guide bars 310 into contact with the anterior face 152, as described previously with respect to the cutting guide block 172 and the hexagonal mounting bars 246 and 248, placing the cutting guide block 304 close to the femur to guide the surgeon in cutting away a portion of the distal end of the femur.

Once the saw cut guided by the saw guiding face 306 has been made through the distal end of the femur as described above with respect to the guide block 12 and the guide block 172, if trial placement of the femur portion of the prosthetic joint shows that the saw cut is incorrectly located or that the resulting surface of the distal end of the femur is improperly oriented, the hexagonal mounting bars 310 can be removed from the guide block 304 and both mounting bars 310 can be rotated through an equal angle, as described above with respect to the guide block 172, to relocate the guide block 304 to a revised position to guide another cut parallel to the first cut.

Alternatively, the original guide block 304 can be replaced either by an adjustment guide block 340, shown in FIGS. 19 and 20, to adjust the angle of extension of the prosthetic joint in an anterior or a posterior direction, or by an adjustment guide block 342, shown in FIGS. 21 and 22, to correct the orientation of the sawed surface of the distal end of the femur with respect to the varus/valgus angle. Such an adjustment block 340 or 342 may be put into position over the same hexagonal mounting bars 310, in place of the original cutting guide block 304.

The adjustment guide block 340 as shown in FIGS. 19 and 20 is symmetrical about a horizontal plane, except for the orientation of its saw guiding face 344. In the adjustment block 340 the saw guiding face 344 is oriented at an anterior/posterior adjustment angle 346 of 3 degrees in the anterior direction relative to the orientation of the saw guiding face 306 of the mounted cutting guide block 304, as indicated by the legend, "A3.degree." visible in an upright orientation in FIG. 19 at 348. At the same time, a legend "P3.degree." is visible inverted at 350 in FIG. 19. With the adjustment cutting guide block 340 inverted, as by rotation about an imaginary longitudinal horizontal axis 352 before being slid down onto the hexagonal mounting bars 310, the adjustment angle 346 would be effective to adjust the cut by 3 degrees in the posterior direction.

A set of adjustment cutting guide blocks in a desired number of different angular variations may be provided so as to establish, for example, one degree, two degrees, three, four, or five degrees of angular variation from the original orientation of the saw guiding face 306 of the cutting guide block 304, and the saw guiding face 344 of each may be marked as at 348 and 350, with a corresponding legend to indicate the direction and the size of the angle 346 provided by each such adjustment cutting guide block of a set.

Similarly, in the adjustment cutting guide block 342, an adjustment angle 352 of 3 degrees toward the left from the orientation of the saw guiding face of the original cutting guide block 304 as mounted on the hexagonal mounting bars 310 is provided by the orientation of the saw guiding face 354, as shown by the upright and legible legend reading, "L 3.degree.," at 356 on the saw guiding face 354 as shown in FIG. 21. Inversion of the adjustment cutting guide block 342 about the longitudinal horizontal axis 358 before mounting it on the hexagonal mounting bars 310 would result in the direction of the angle 352 being reversed, as would be indicated by the legend, "R 3.degree." at 360 in FIG. 21 then being upright and legible to the surgeon. Each adjustment guide block 342 is labeled, as by being engraved with the appropriate letter R or L and the appropriate number of degrees, so that when each block is in place on the hexagonal mounting bars the angle and direction of orientation of the adjustment saw guiding face 354 are legible in view of the surgeon. The upper and lower surfaces 362 and 364 of each of the cutting guide blocks 340 and 342 are similar, so that inversion of either of the cutting guide blocks 340 and 342 makes no difference in the way the cutting guide block 340 or 342 rests upon the distal end of the femur.

As shown in FIG. 23, a preliminary fixation screw 366 with a main body 368 of such a size that it fits slidably within the intramedullary pin bore 338 in a swivel block 334 has a threaded outer end 370 which can be engaged in a hole drilled in the distal end of the femur in the appropriate location, which is readily identifiable by the surgeon. Once the threaded outer end 370 is firmly engaged in the femur, the compression spring 372, located between the shoulder 374 and the swivel block 334 then urges the alignment body 262 toward the distal end of the femur while the varus/valgus adjustment pins 322 and 324 are adjusted to orient the alignment body correctly with respect to varus or valgus. While the slots 316 and holes 318 and 320 are available in the alignment body 262, the surgeon may choose to use fixation pins in none or only a few of those holes or slots to hold the alignment body 262 more or less fixedly in position on the distal end of the femur while the positions are determined for drilling holes into the anterior face 152 of the distal end of the femur through the mounting pin holes 312 defined in the hexagonal mounting bars 310.

In a distal femoral cutting guide assembly 368 which is an alternative embodiment of the device, as shown in FIGS. 24-30, a guide block locating arm 370 may be attached to the support member 270', which is generally similar to the previously described support member 270, to support a cutting guide block 372 that is removably attached to the guide block locating arm 370. The guide block locating arm 370 may be attached to and clamped to the support member 270' at a selected height relative to the alignment body 262 from which the support member 270' extends upward, by a sliding support assembly whose function is similar to that of the slide assembly 276 described above with respect to the distal femoral cutting guide assembly 260. The sliding support assembly includes a slide body 373 having a central portion 374 fitting slidably, but not rotatably, in the slot 282 defined by the upwardly extending support member 270'. The central portion 374 thus maintains a selected angular relationship of the slide body 373 with the support member 270'. A support block portion 375 of the slide body 373 extends medially outward beyond the medial face 286 of the support member 270' and may be pressed against shoulders 376 between rails 377 on the medial side of the support member 270' by tightening a clamping screw 378 in a threaded bore 379, as shown best in FIG. 28. The clamping screw 378 may have its head countersunk in a clamping plate 380, and the clamping screw 378 extends through a bore 381 to mate with the threaded bore 379 in the central portion 374 of the slide body 373 to clamp the slide body 373 to the support member 270' at a selected height. The clamping plate 380 may be disposed slidably on the shoulders 300 and between the rails 302 on the lateral side of the support member 270' in the same manner as the nut 298 described previously. The support block portion 375 holds the guide block locating arm 370 may thus be kept at a constant angle 382, such as 90 degrees, to the support member 270', as will be explained in greater detail presently.

The cutting guide block 372 is attached to a rear end portion 383 of the locating arm 370, so that the cutting block 372 is located closely adjacent to the main portion of the guide block locating arm 370, which may have the form of a long narrow oval including a top member 384 and a bottom member 386 which are parallel with each other. As shown best in FIG. 26, a long depth adjustment screw 388 extends parallel with and between the top and bottom members 384 and 386, with a rear end of the screw 388 supported rotatably in a bearing 390 at the rear end of the locating arm 370. A near or front end of the depth adjustment screw 388 extends through a bore 392 defined in the front end of the guide block locating arm 370, and a suitable arrangement is provided to support the depth adjustment screw 388 with respect to thrust forces. For example, a circumferential groove 394 may be defined in a front end portion of the screw 388, and a grub screw 396 may be mounted in a corresponding threaded bore in the locating arm 370 so as to have a rounded tip of the screw 396 engaged in the groove 394 to keep the depth adjustment screw 388 from moving longitudinally in the locating arm 370.

An adjustment knob 398 is attached to the front end of the depth adjustment screw 388 to rotate the adjustment screw 388. The adjustment screw 388 is mated in a threaded bore 400 in the support block portion 375 of the slide body 373, as shown best in FIG. 28, and thus keeps the guide block locating arm 370 closely alongside the medial face 286 of the support member 270'. The threaded bore 400 is parallel with the medial face 286 of the support member 270' and with top and bottom surfaces 402 and 404 of the support block portion 375. The top and bottom surfaces 402 and 404 may be in sliding relationship to inner surfaces of the top and bottom members 384 and 386 of the guide block locating arm 370 to help keep it oriented at the angle 382 to the support member 270'. Rotation of the adjustment screw 386 thus moves the guide block locating arm 370 rearward or forward alongside the support member 270', to carry the cutting guide block 372 to a desired depth relative to the support member 270'.

As a useful indication of the position or the amount of adjustment of the depth of the cutting guide block 372 while the location of the cutting guide block 372 is being established with respect to a patient's femur, indicia 405 may be provided at useful intervals on the top member 384 of the guide block locating arm 370. For example a line may be provided at each millimeter, with a label for each five millimeters, to indicate a position of the guide block locating arm 370 relative to the support member 270.

The cutting guide block 372, shown also in FIGS. 29 and 30, may be similar in most ways to the cutting guide block 172, shown in FIGS. 9-12. Instead of being attached to the guide block locating arm 370 by a fastening screw 186, which may not be easily accessible when it is desired to release the cutting guide block 372 from the locating arm 370, the cutting guide block 372 may be connected to the rear end portion 383 securely, yet removably by a detent, such as a spring loaded ball detent 406 that may be mounted in a threaded bore 408 in the bottom of the cutting guide block 372 so that the ball protrudes up into the receptacle 409 in the guide block 372. A corresponding dimple 410 may be provided in the rear end portion 383 of the guide block locating arm 370 to receive the spring-loaded ball when the cutting guide block 372 is mounted on the locating arm 370.

A procedure for using the distal femoral cutting guide assembly 368 is similar to that for using the cutting guide assembly 260, shown in FIGS. 14-23, with the alignment body 262 being mounted on the femur, and adjusted about its longitudinal axis, and then adjusted for varus/valgus. Next the support member 270' may be placed at the desired angle 272 about a transverse extension/flexion axis, and the slide body 373 may then be set and clamped at the required height along the support member 270'. The knob 398 may then be turned to rotate the depth adjustment screw 388 as needed to move the support arm 370 rearward to the required depth position for the guide block 372. Then, once the cutting guide block 372 is pinned to the femur 140 by pins 156 through the bores 250, 252 in the mounting bars 246, 248 the alignment body 262 may be released from the femur, and rear end portion 383 may be disconnected from the guide block 372 by overcoming the ball detent and retracting the rear end portion 382 from the receptacle 409.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method of preparing a distal end of a femur for knee surgery comprising:
   (a) providing a distal femoral cutting guide, said distal femoral cutting guide includes:
   an alignment body defining a laterally oriented slot and a locating pin hole spaced apart from said slot, said slot defining a horizontal plane and both said slot and said pin hole extending through said alignment body from a front face to a rear face thereof; wherein said laterally oriented slot is adapted for lateral adjustment but not rotational adjustment of said alignment body with respect to the distal end of the femur;
   a varus/valgus adjustment member mated adjustably with and protruding rearwardly an adjustable distance from said alignment body; wherein said varus/valgus adjustment member is mated adjustably with said alignment body in a location that is separate from said locating pin hole;
   a support member connected with and extending upwardly from a lower portion of said alignment body; wherein said support member is adapted to form a user selected angle with respect to said alignment body;
   a guide block locating arm adjustably attached to said support member and extending rearwardly therefrom;
   a guide block detachably carried on a rear end of said guide block locating arm;
   (b) placing said alignment body in a selected location adjacent a distal end portion of said femur;
   (c) forming a hole extending into said femur and aligned with said horizontal slot;
   (d) placing a first locating pin through said horizontal slot and so that it extends into said hole extending into said femur;
   (e) establishing a varus/valgus alignment of said alignment body by placing an end of said varus/valgus adjustment member into contact against said femur so as to support said alignment body in an aligned position with respect to said distal end of said femur;
   (f) forming a second hole extending into said femur and aligned with said locating pin hole;
   (g) placing a second locating pin through said locating pin hole so as to extend into said second hole in said femur;
   (h) thereafter, securing said alignment body to said femur in a said aligned position by forming a third hole extending into said femur in a location aligned with a corresponding locating pin hole oriented at an oblique angle with respect to said second alignment pin and placing a third locating pin so as to extend through said corresponding locating pin hole in said alignment body and into said third hole in said femur;
   (i) supporting a cutting guide block on a locating arm adjustably attached to said alignment body;
   (j) positioning said cutting guide block relative to said alignment body, to bring a guiding face of said cutting guide block into a predetermined orientation and position with respect to said alignment body;
   (k) connecting said cutting guide block to an anterior face of said distal end portion of said femur so as to hold said guiding face in said predetermined orientation;
   (l) removing said alignment body and said locating arm from said femur and said cutting guide block, leaving said cutting guide block adjacent said anterior face of said distal end of said femur with said guiding face in said predetermined orientation and leaving an unobstructed cutting plane through said distal end of said femur defined by said guiding face of said cutting guide block; and
   (m) thereafter, using said guiding face to guide a cutting tool to remove a part of said distal end portion.

2. The method of claim 1 wherein said alignment body defines a central through-hole extending therethrough from a front face to a rear face of said alignment body, wherein the step of placing said alignment body in a selected location includes placing said alignment body where an intramedullary rod fitted in an intramedullary canal of said femur extends through said central through-hole when said alignment body is in said selected location.

3. The method of claim 2 wherein said alignment body includes a swivel located in said central through-hole, said swivel defining a bore extending through said central through-hole and said swivel establishing a vertical axis parallel with said rear face of said alignment body and intersecting said bore, and wherein said step of placing said alignment body in a selected location includes locating said alignment body where said intramedullary rod extends through said bore defined by said swivel.

4. The method of claim 1 wherein said support member includes a height adjustment slot, and including the step of using a fastener extending from said height adjustment slot to hold said locating arm in a position at a selected height with respect to said support member.

5. The method of claim 1 including the step of adjusting a position of said locating arm in a direction parallel with a longitudinal axis of said femur.

6. The method of claim 5 including providing indicia on said locating arm and using said indicia to locate a planar saw guiding face of said guide block at a desired distance from said alignment body when said guide block is mounted on said locating arm.

7. The method of claim 1 wherein said alignment body includes a second said slot establishing a respective horizontal plane, and including the steps of forming a hole in said femur aligned with said second slot and placing a locating pin through said second slot into said femur.

8. The method of claim 1, including inserting a locating pin into said femur through a second slot extending from a front face to a rear face of said alignment body and oriented parallel with said horizontal plane prior to said step of performing a varus/valgus adjustment.

9. The method of claim 1 including the further step of thereafter inserting at least one said locating pin into said femur through a locating pin hole oriented parallel with said horizontal plane and at an oblique angle with respect to said rear face of said alignment body.

10. The method of claim 1 including the step of providing a plurality of pairs of mounting pin holes in said cutting guide block, the holes of each said pair being spaced apart from each other by an equal distance and the mounting pin holes all being aligned parallel with said guiding face, and performing said step of connecting by inserting respective mounting pins through both of a pair of said mounting pin holes so as to extend into said anterior face.

11. The method of claim 10 wherein said pairs of mounting pin holes are located at different distances from said guiding face, including the further step of thereafter moving said cutting guide block to a selected location with respect to said distal end portion of said femur by sliding said cutting guide block off said mounting pins and placing said cutting guide block adjacent said anterior face with said mounting pins extending through the holes of another one of said pairs.

12. The method of claim 1 wherein the step of connecting said cutting guide block to said anterior face includes inserting a pair of mounting pins into respective mounting pin holes in said distal end portion through respective mounting pin holes defined in a pair of mounting bars fitted in respective mounting bar holes in said cutting guide block, including the additional step of adjusting the position of said cutting guide block with respect to said distal end portion by similarly reorienting each of said pair of mounting bars in said respective mounting bar holes in said cutting guide block, so as to move said cutting guide block with respect to said pair of mounting pins with said pair of mounting pins left extending through respective mounting pin holes defined in said mounting bars and thence extending further into said respective mounting pin holes in said anterior face of said distal end portion of said femur.

13. The method of claim 12 including the additional step of removing the cutting guide block from said mounting bars and mounting on said mounting bars an adjustment cutting guide block having an adjustment guiding face, with said adjustment guiding face oriented at a selected acute angle with respect to an orientation of said guiding face of said cutting guide block when said cutting guide block is mounted on said mounting bars.

14. The method of claim 1 wherein said step of connecting said cutting guide block to an anterior face includes inserting a pair of mounting pins through respective mounting pin holes in said cutting guide block into respective mounting pin holes in said anterior face of said distal end portion of said femur, and including the additional step of thereafter removing the cutting guide block from said mounting pins and mounting on said mounting pins an adjustment guide block having an adjustment guiding face with said adjustment guiding face oriented at a selected acute angle with respect to said predetermined orientation of said guiding face of said cutting guide block when said cutting guide block is connected to said anterior face by said mounting pins.

15. The method of claim 1 including the step of inserting a spring-loaded attachment screw through an aperture in the alignment body and into said femur, thereby fastening the alignment body to the distal end of the femur in an initial position, prior to adjusting varus/valgus.

16. The method of claim 1 wherein the step of positioning said cutting guide block relative to said alignment body includes turning an adjustment screw to move said cutting guide block to a location at a selected distance rearward from a support member to which said locating arm is attached.

* * * * *